US011974765B2

(12) United States Patent
Ibarra et al.

(10) Patent No.: US 11,974,765 B2
(45) Date of Patent: May 7, 2024

(54) DEVICE AND METHOD FOR TREATING NOSEBLEEDS

(71) Applicants: Matthew James Ibarra, Cerritos, CA (US); Christopher Chang, Beverly, MA (US)

(72) Inventors: Matthew James Ibarra, Cerritos, CA (US); Christopher Chang, Beverly, MA (US)

(*) Notice: Subject to any disclaimer, the term of this patent is extended or adjusted under 35 U.S.C. 154(b) by 399 days.

(21) Appl. No.: 17/158,323

(22) Filed: Jan. 26, 2021

(65) Prior Publication Data
US 2022/0160384 A1  May 26, 2022

Related U.S. Application Data

(63) Continuation-in-part of application No. 16/242,213, filed on Jan. 8, 2019, now Pat. No. 10,925,608.

(51) Int. Cl.
*A61B 17/24* (2006.01)

(52) U.S. Cl.
CPC .................. *A61B 17/24* (2013.01)

(58) Field of Classification Search
CPC .......... A61C 5/90; A61B 17/132; A61B 17/24
See application file for complete search history.

(56) References Cited

U.S. PATENT DOCUMENTS

| 4,337,765 A | 7/1982 | Zimmerman |
| 5,516,286 A * | 5/1996 | Kushner .................. A61C 5/90 433/136 |
| 5,601,093 A | 2/1997 | Sheehan |
| 2004/0194788 A1 | 10/2004 | Sweet |
| 2006/0237020 A1 | 10/2006 | Morgan et al. |
| 2008/0193897 A1 | 8/2008 | Kubo et al. |
| 2009/0165805 A1 | 7/2009 | Syrop et al. |
| 2012/0085354 A1 | 4/2012 | Polk, III |
| 2013/0048532 A1 | 2/2013 | Rix |
| 2013/0298917 A1 * | 11/2013 | Poisson ................ A63B 71/085 128/861 |
| 2014/0261465 A1 | 9/2014 | Turkbas |
| 2016/0338684 A1 | 11/2016 | Arden et al. |

* cited by examiner

*Primary Examiner* — Jocelin C Tanner
(74) *Attorney, Agent, or Firm* — AKC PATENTS, LLC; Aliki K. Collins

(57) ABSTRACT

A mouth insert for treating nosebleeds includes a main body and a bite tab. The bite tab removably engages the main body and is configured to move up and/or down vertically in order to adjust the height of the device. The main body includes a horizontally extending elongated portion, a center portion extending downward from a bottom surface of the elongated portion, and the center portion has a narrower width than the horizontally extending elongated portion. The elongated portion of the main body is shaped and dimensioned to be inserted into a buccal cavity of a user's mouth and to fit behind the user's upper lip and in front of the user's upper gums, and the center portion is shaped and dimensioned to be positioned only in front of the user's upper front teeth. The bite tab includes a horizontally extending portion and a vertically extending portion and the vertically extending portion is configured to removably engage the center portion of the main body and the horizontally extending portion includes a push-surface used for pushing the device upward in order to provide pressure to the user's nose.

19 Claims, 20 Drawing Sheets

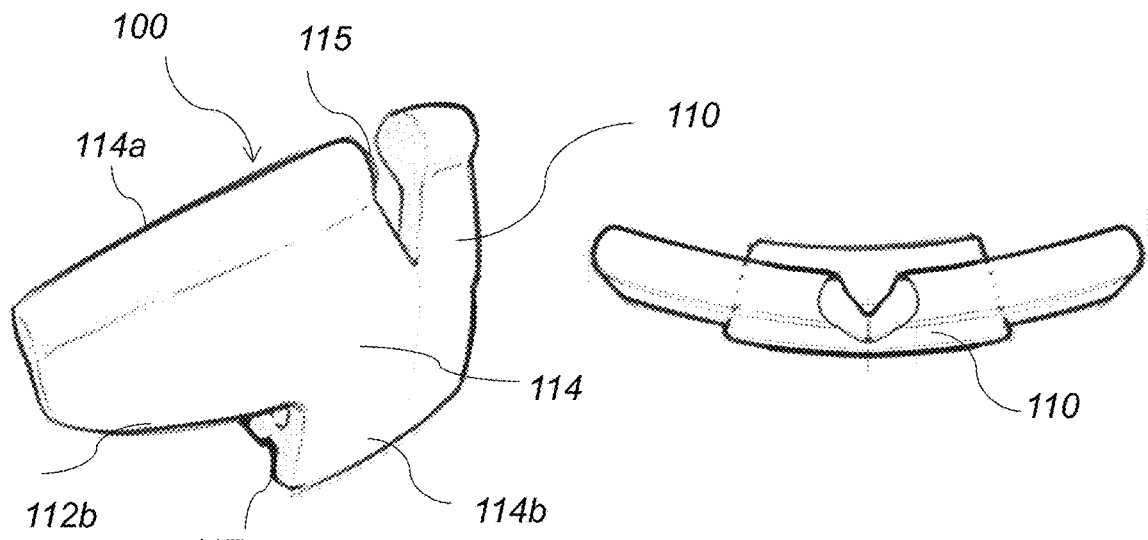
FIG. 3A
FIG. 3B
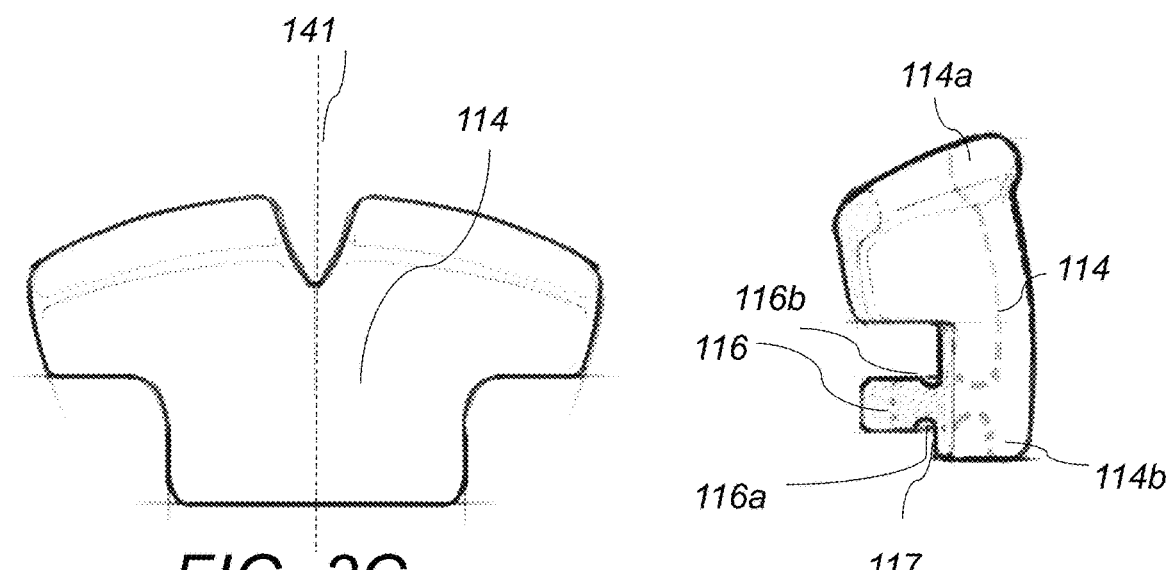
FIG. 3C
FIG. 3D

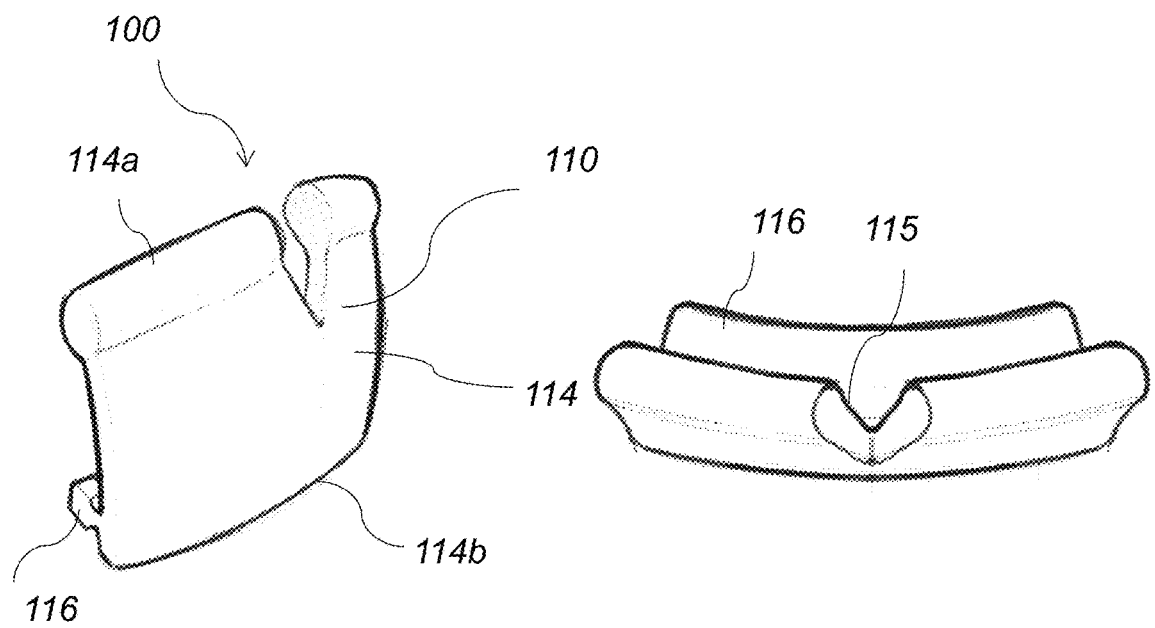
FIG. 4A
FIG. 4B
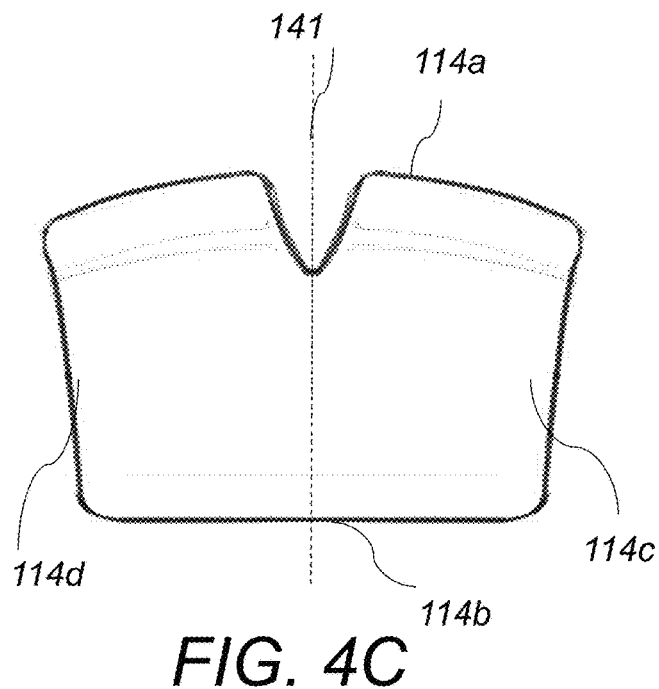
FIG. 4C
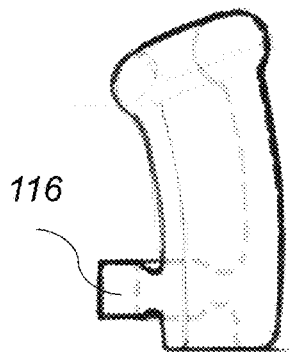
FIG. 4D

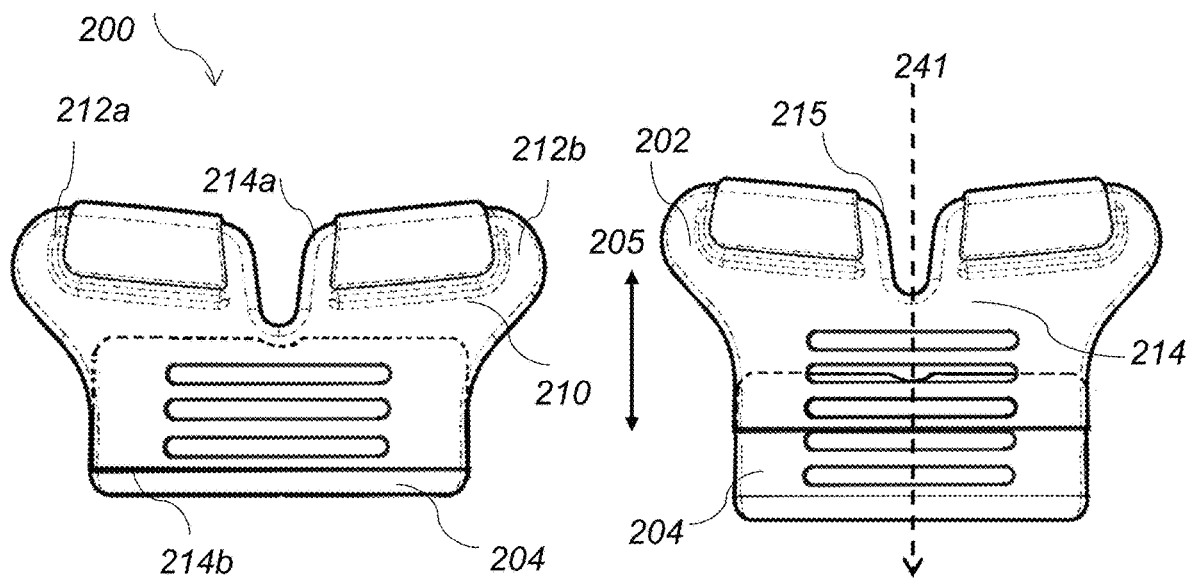
FIG. 13A
FIG. 13B
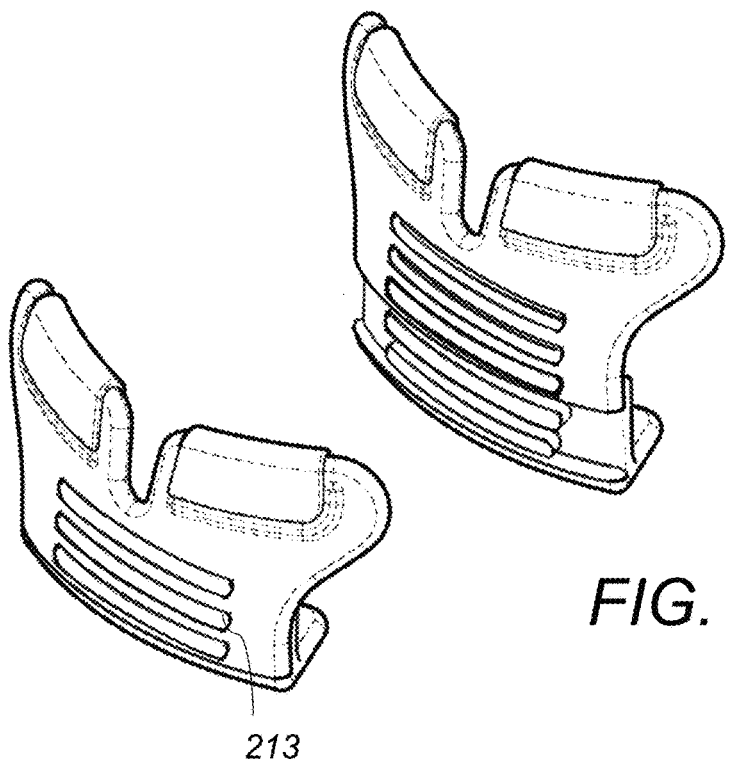
FIG. 13C
FIG. 13D

DEVICE AND METHOD FOR TREATING NOSEBLEEDS

CROSS REFERENCE TO RELATED CO-PENDING APPLICATIONS

This application is a continuation-in-part and claims the priority to and benefit of U.S. patent application Ser. No. 16/242,213 filed on Jan. 8, 2019 and entitled DEVICE AND METHOD FOR TREATING NOSEBLEEDS, which is commonly assigned and the contents of which are expressly incorporated herein by reference.

FIELD OF THE INVENTION

The present invention relates to a device and a method for treating nosebleeds, and more particularly to a device and a method for stopping or slowing nosebleeds in humans by applying pressure under the upper lip of a user.

BACKGROUND OF THE INVENTION

A typical method for treating nosebleeds or epistaxis in a patient includes positioning the patient upright, leaning forward slightly and firmly pinching the outside of the nose with the thumb and index fingers just below the bone against the face. Other methods include applying cold packs, cauterization, nasal packing or even surgery. However, pinching the nose, cauterization, nasal packing and surgery usually cause discomfort and pain to the patient. Therefore, there is a need for a non-invasive, painless and simple technique for stopping nosebleeds.

SUMMARY OF THE INVENTION

In general, in one aspect, the invention features a device for treating nosebleeds including a mouth insert comprising a main body and a bite tab. The bite tab removably engages the main body and is configured to move up and/or down vertically in order to adjust the height of the device. The main body comprises a horizontally extending elongated portion, a center portion extending downward from a bottom surface of the elongated portion, and the center portion comprises a narrower width than the horizontally extending elongated portion. The elongated portion of the main body is shaped and dimensioned to be inserted into a buccal cavity of a user's mouth and to fit behind the user's upper lip and in front of the user's upper gums, and the center portion is shaped and dimensioned to be positioned only in front of the user's upper front teeth. The bite tab comprises a horizontally extending portion and a vertically extending portion and the vertically extending portion is configured to removably engage the center portion of the main body and the horizontally extending portion comprises a push-surface used for pushing the device upward in order to provide pressure to the user's nose.

Implementations of this aspect of the invention may include one or more of the following features. The vertically extending portion of the bite tab comprises protrusions that are shaped and sized to fit within and engage slots formed on the center portion of the main body. The vertically extending portion of the bite tab is shaped and sized to fit within a cutout opening formed on the center portion of the main body. The vertically extending portion of the bite tab comprises teeth on a left side and a right side and the teeth of the vertically extending portion are shaped and sized to engage teeth formed on a left side and a right side of the cutout opening of the center portion of the main body, respectively. The teeth of the vertically extending portion comprise a flat and horizontal portion that prevents upward motion of the bite tab while in use. The bite tab further comprises left and right finger extensions that are shaped and sized to fit within and engage notches formed on a left side and a right side of a cutout opening of the center portion of the main body, respectively. Each finger extension protrudes forward and downward at an angle and comprises a dowel bent at 90° degrees. The vertically extending portion of the bite tab comprises pin dowels that are shaped and sized to fit into pin openings formed on the center portion of the main body. The vertically extending portion of the bite tab comprises a left component and a right component that are shaped and sized to fit within a left cutout opening and a right cutout opening formed on the left side and the right side of the center portion of the main body, respectively. The left and right components of the vertically extending portion of the bite tab comprise rib grooves that are shaped and sized to engage rib tracks formed on the left cutout opening and the right cutout opening of the center portion of the main body, respectively. The bite tab further comprises a pawl extending from the horizontally extending portion of the bite tab and being angled upwardly, and the pawl comprises a pawl head shaped and sized to engage a protrusion on the center portion of the main body. The bite tab further comprises a center cutout in the horizontally extending portion and left and right finger extensions protruding from left and right edges of the center cutout of the bite tab, and the left and right finger extensions are shaped and sized to fit within and engage left and right notches formed on left and right sides of a center cutout of the center portion of the main body. The bite tab further comprises left and right outer extensions protruding forward from the horizontally extending portion of the bite tab and the left and right outer extensions are shaped and sized to be placed around left and right sides of the center portion of the main body. The elongated portion of the main body comprises a U-shaped gap dimensioned to fit around the user's frenulum. The elongated portion and the center portion of the main body are curved backwards and have a curvature radius that matches the user's upper gum line radius. The elongated portion of the main body comprises an adjustable width. The elongated portion of the main body comprises cut-away features on left and right sides of the elongated portion and the cut-away features are designed to tear off and thereby to reduce the width of the device. The elongated portion of the main body comprises foldable extensions on left and right sides of the elongated portion and the foldable extensions are designed to unfold and thereby to increase the width of the device.

In general, in another aspect, the invention features a method for treating nosebleeds including the following. First, providing a mouth insert comprising a main body and a bite tab. The bite tab removably engages the main body and is configured to move up and/or down vertically in order to adjust the height of the device. The main body comprises a horizontally extending elongated portion, a center portion extending downward from a bottom surface of the elongated portion, and the center portion comprises a narrower width than the horizontally extending elongated portion. The elongated portion of the main body is shaped and dimensioned to be inserted into a buccal cavity of a user's mouth and to fit behind the user's upper lip and in front of the user's upper gums, and the center portion is shaped and dimensioned to be positioned only in front of the user's upper front teeth. The bite tab comprises a horizontally extending portion and a vertically extending portion and the vertically extending portion is configured to removably engage the center portion of the main body and the horizontally extending portion comprises a push-surface. Next, inserting the mouth insert into a buccal cavity of a user's mouth and then placing a user's tongue, teeth, or finger onto the push-surface and applying pressure upward to the user's buccal cavity and towards an anterior portion of the user's nose.

Among the advantages of this invention may be one or more of the following. The invention provides a device and a method for stopping or slowing a nosebleed without medications, invasive operations, contact with the nasal passages or pain to the patient.

The details of one or more embodiments of the invention are set forth in the accompanying drawings and description below. Other features, objects and advantages of the invention will be apparent from the following description of the preferred embodiments, the drawings and from the claims.

BRIEF DESCRIPTION OF THE DRAWINGS

Referring to the figures, wherein like numerals represent like parts throughout the several views:

FIG. 3A is a perspective view of a second embodiment of the device for treating nosebleeds according to this invention;

FIG. 3B is a top view of the device of FIG. 3A;

FIG. 3C is a front view of the device of FIG. 3A;

FIG. 3D is a side view of the device of FIG. 3A;

FIG. 4A is a perspective view of a third embodiment of the device for treating nosebleeds according to this invention;

FIG. 4B is a top view of the device of FIG. 4A;

FIG. 4C is a front view of the device of FIG. 4A;

FIG. 4D is a side view of the device of FIG. 4A;

FIG. 13A is a front view of another embodiment of the device for treating nosebleeds according to this invention;

FIG. 13B is a front view of the embodiment of the device for treating nosebleeds of FIG. 13A with the bite tab moved down;

FIG. 13C is a front perspective view of the embodiment of the device for treating nosebleeds of FIG. 13A;

FIG. 13D is a front perspective view of the embodiment of the device for treating nosebleeds of FIG. 13A with the bite tab moved down;

DETAILED DESCRIPTION OF THE INVENTION

Figure 1A:
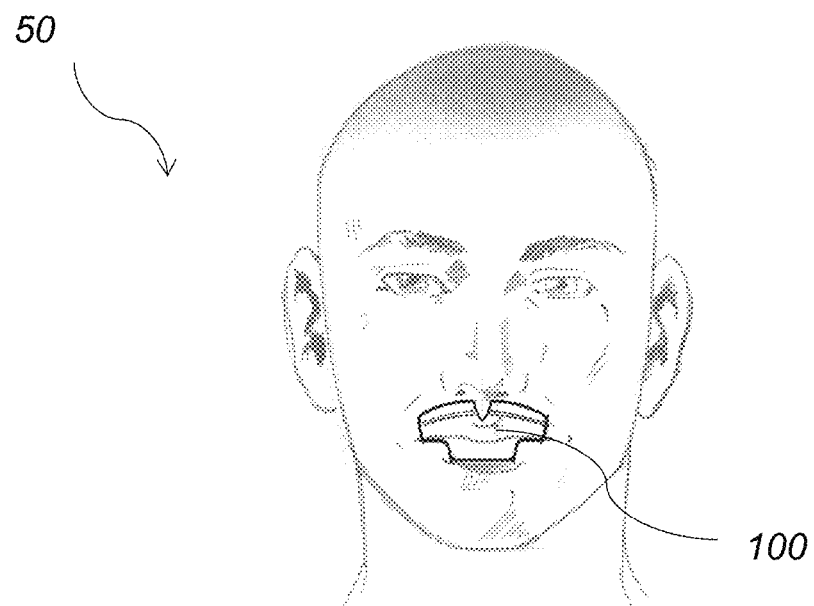
FIG. 1A is a front view of a user with a device according to this invention inserted inside the user's mouth under the upper lip.
Figure 1B:
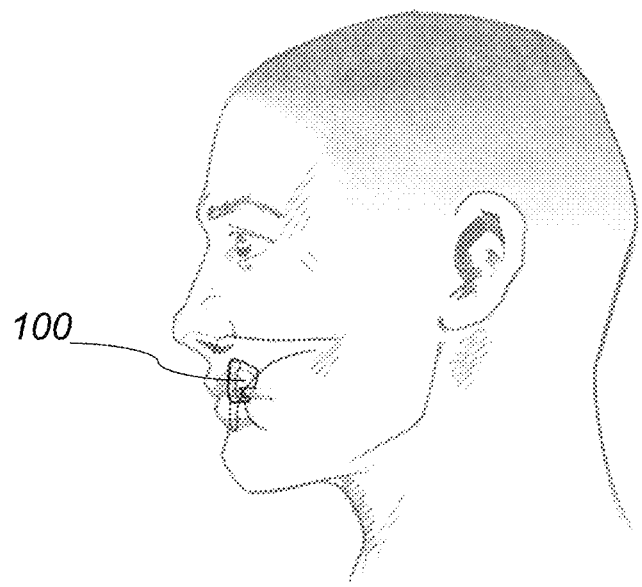
FIG. 1B is a side view of the user of FIG. 1A with the device according to this invention inserted inside the user's mouth under the upper lip.

Referring to FIG. 2A-FIG. 2D, a device 100 for treating nosebleeds includes an elongated body 110, shaped and dimensioned to be inserted into the buccal cavity of a user's 50 mouth and to fit behind the user's upper lip and in front of the user's upper gums, as shown in FIG. 1A. The top portion of device 110 includes a gap 115 extending along the midline 141. Gap 115 has a V-shape and is dimensioned to fit around the user's frenulum, without interfering with the frenulum, which is located at the sagittal plane and top of the gum line. Elongated body 110 includes a central portion 114 having a top 114a, a bottom 114b and left and right portions 112a, 112b that extend sidewise from the central portion 114. Top 114a, has a cylindrical cross section and together with the central portion 114 curves backwards and has a curvature radius that matches the radius of the user's upper gum line. Bottom 114b extends backwards and forms a "bite" tab 116. The central portion 114 is shaped and dimensioned to be positioned in front of the user's upper front teeth and the bite tab 116 is shaped and dimensioned to provide a biting surface for the user's upper front teeth. In this case, the central portion 114 and the bite tab 116 form a structure that has the shape of a J-hook and wraps around the user's front top teeth, as shown in FIG. 1B. Left and right portions 112a, 112b are shaped and dimensioned to fit the user's left and right sides of the upper gums, respectively.

In operation, the user 50 inserts the device 100 in the mouth and places the elongated body 110 behind the upper lip and in front of the top gums, while the bite tab 116 wraps around the top teeth. Next, the user bites down on the bite tab 116 and the biting action causes the top 114a and the central portion 114 to apply pressure upward towards the anterior portion of the nose. The applied pressure blocks the blood flow to the nose and the anterior arteries and causes device 100 to act as a tourniquet that reduces and stops nosebleeds.

As was mentioned above, the elongated body 110 is shaped and dimensioned to be inserted into the buccal cavity of a user's 50 mouth and to fit behind the user's upper lip and in front of the user's upper gums, as shown in FIG. 1A. In one example, device 100 is dimensioned to fit an adult user's mouth and has a width W in the range of 2-3 inches and a height H in the range of ¾ to 1¼ inches. The thickness of the material T is in the range of ⅛ to ¼ inches. Gap 115 has a width w1 in the range of ¼ to ½ inches and a height h1 of about ½ inch. Bite tab 116 extends from front to back by a distance D that is in the range of ½ to 1 inch. Children sizes of the tourniquet device 100 typically range 50-70% of the above mentioned approximate sizes.

A package of several tourniquet devices is provided that includes several comfortable size options for men, women, and children. Alternatively, a single large device 100 is provided that has adjustable width W to fit users with various mouth sizes. In this case, device 100 includes cut-away features or extensions 118 on the left and right portions 112a, 112b, as shown in FIG. 2C. Cut away features 118 are designed to tear off and thereby to shrink the width of the device so that it fits a user with a smaller mouth. Extensions 118 are unfolded to enlarge the width of the device to accommodate a user with a larger mouth.

Device 100 is made of semi-rigid materials including silicone, latex, rigid and flexible polypropylene, cotton gauze, other forms of cotton, or pressed paper molds, among others. Elongated body 110 may be provided in a straightened form and may be bendable to conform to the user's mouth curvature. Alternatively, elongated body 110 may be provided in an already backwards-curved form. The entire device 100 may be flexible or rigid. In cases where device 100 is rigid it may still retain some flexibility to be able to conform to the user's mouth anatomy. The outer surfaces of the elongated body 110 are usually smooth and the edges and corners are rounded in order to provide a comfortable feel while being in contact with the user's gums and tissue and to prevent discomfort, pain or damage of the user's gums.

Referring to FIG. 3A-FIG. 3D, in another embodiment, device 100 for treating nosebleeds includes an elongated body 110, shaped and dimensioned to be inserted into the buccal cavity of a user's 50 mouth and to fit behind the user's upper lip and in front of the user's upper gums, as shown in FIG. 1A. The top portion of device 110 includes a gap 115 in the midline. Gap 115 is shaped and dimensioned to fit around the user's frenulum, so that it does not interfere with the frenulum, which is located at the sagittal plane and top of the gum line. Elongated body 110 includes a central portion 114 having a top 114a, a bottom 114b and left and right portions 112a, 112b that extend sidewise. Top 114a, has a cylindrical cross section and together with the central portion 114 curves backwards and has a curvature radius that matches the radius of the user's upper gum line. Bottom 114b extends downwards from the central portion 114 and has a backwards extending "bite" tab 116. The central portion 114 is shaped and dimensioned to be positioned in front of the user's upper front teeth and the bite tab 116 is shaped and dimensioned to provide a biting surface for the user's front teeth. Bite tab 116 is formed at a distance 117 above the bottom end 114b and includes a semi-circled notch 116a at the bottom surface of tab 116 that extends from the left to the right sides of the central portion 114. Notch 116a provides a bite surface for the bottom teeth of the user to register on the device 100. Bite tab 116 also includes a semi-circled notch 116b at the top surface of tab 116 that is shaped to accommodate the user's top teeth.

Referring to FIG. 4A-FIG. 4D, in another embodiment, a device 100 for treating nosebleeds includes an elongated body 110, shaped and dimensioned to be inserted into the buccal cavity of a user's 50 mouth and to fit behind the user's upper lip and in front of the user's upper gums, as shown in FIG. 1A. The top portion of device 110 includes a gap 115 in the midline. Gap 115 is shaped and dimensioned to fit around the user's frenulum, so that it does not interfere with the frenulum, which is located at the sagittal plane and top of the gum line. Elongated body 110 includes a central portion 114 having a top 114a, a bottom 114b and left and right sides 114c, 114d. Top 114a, has a cylindrical cross section and together with the central portion 114 curves backwards and has a curvature radius that matches the radius of the user's upper gum line. Bottom 114b has a backwards extending "bite" tab 116. The central portion 114 is shaped and dimensioned to be positioned in front of the user's upper front teeth and the bite tab 116 is shaped and dimensioned to provide a biting surface for the user's front teeth. Bite tab 116 is formed at a distance 117 above the bottom end 114b and includes a semi-circled notch 116a at the bottom surface of tab 116 that extends from the left to the right sides of the central portion 114. Notch 116a provides a bite surface for the bottom teeth of the user to register on the device 100. Bite tab 116 also includes a semi-circled notch 116b at the top surface of tab 116 that is shaped to accommodate the user's top teeth. In this case, central portion 114 extends the entire width W of the elongated body 110. Bite tab 116 also extends the entire width of central portion 114 and the elongated body 110 from the left side 114c to the right side 114d and provides a wider bite surface than in the cases of FIG. 2A and FIG. 3A.

Figure 2A:
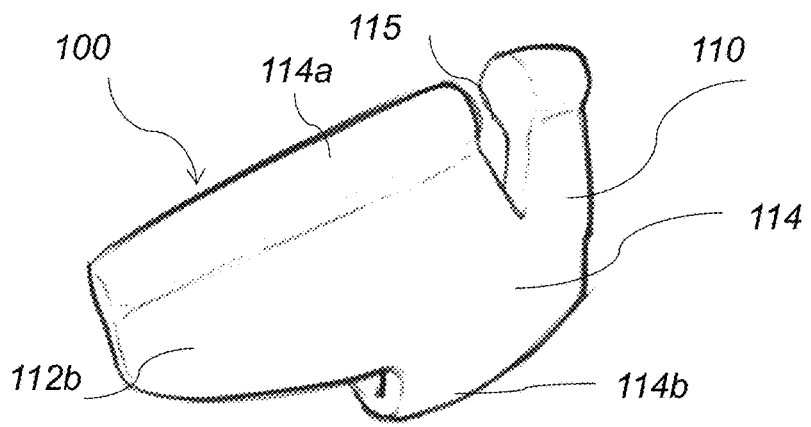
FIG. 2A is a perspective view of a first embodiment of the device for treating nosebleeds according to this invention.
Figure 2B:
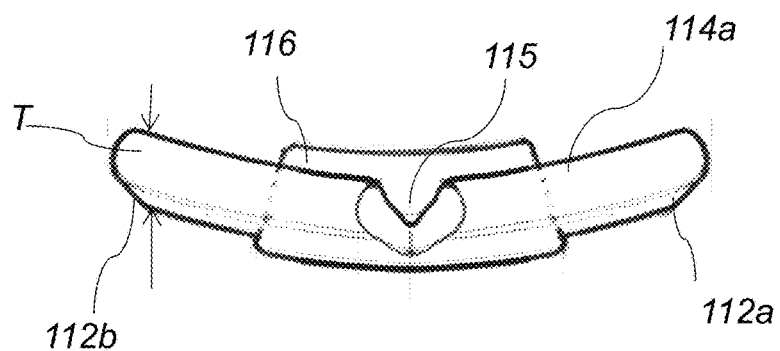
FIG. 2B is a top view of the device of FIG. 2A.
Figure 2C:
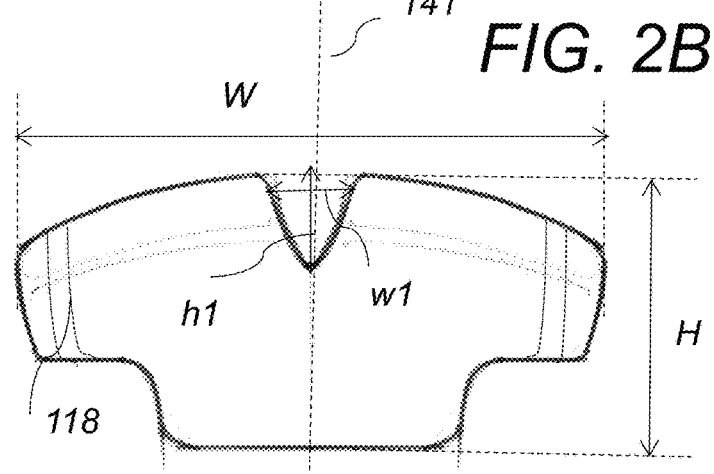
FIG. 2C is a front view of the device of FIG. 2A.
Figure 2D:
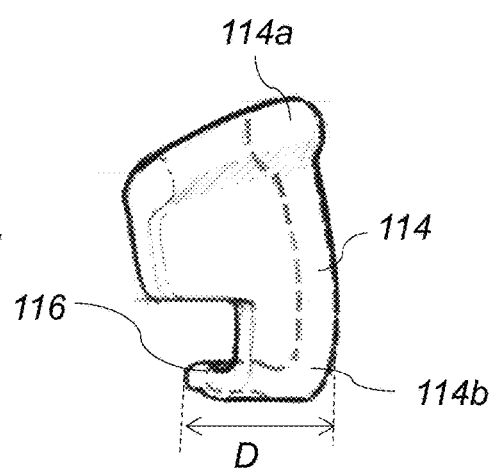
FIG. 2D is a side view of the device of FIG. 2A.
Figure 5:
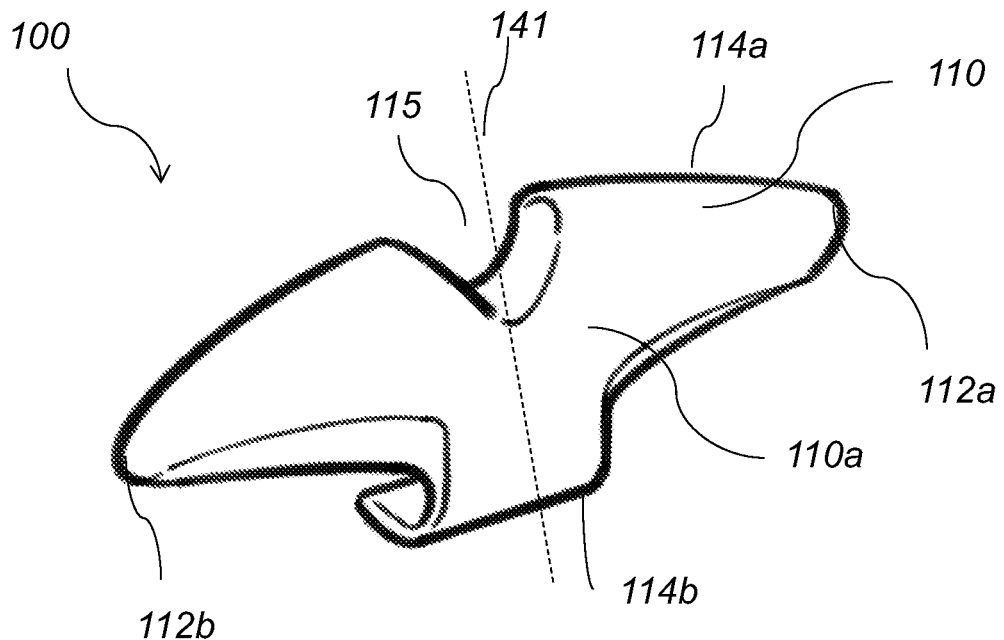
FIG. 5 is a perspective view of a fourth embodiment of the device for treating nosebleeds according to this invention.

Referring to FIG. 5, device 100 has the same geometry and features as device 100 of FIG. 2A. In this case, the front surface 110a is straight from left to right and the thickness of body 110 varies from the top 114a to bottom 114b and at various cross sections from left portion 112a to right portion 112b. Device 100 is made of semi-rigid material and can conform to the anatomy of the user's mouth when placed inside the upper-lip.

Figure 6:
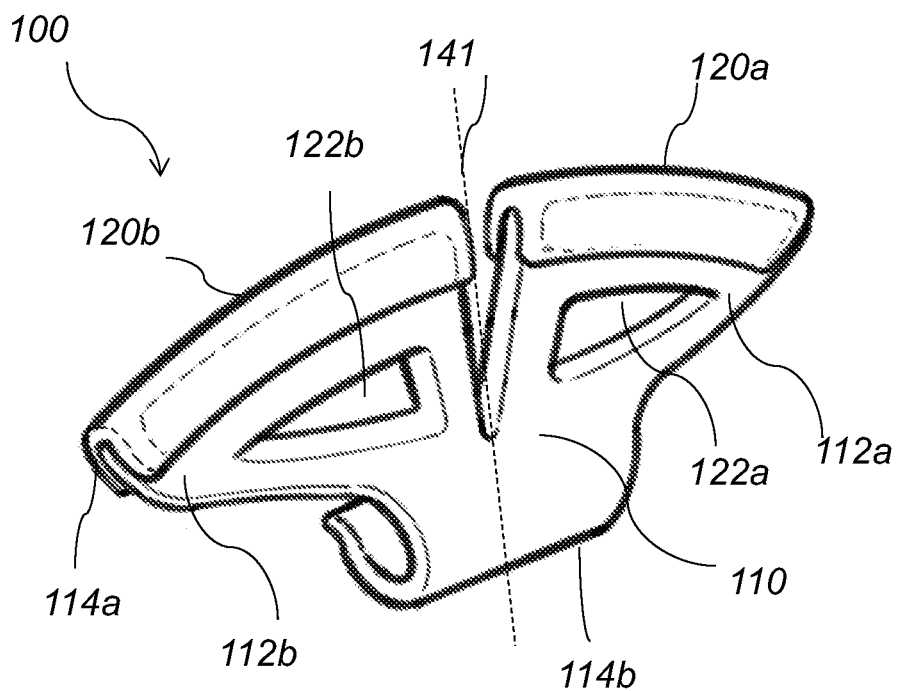
FIG. 6 is a perspective view of a fifth embodiment of the device for treating nosebleeds according to this invention.

Referring to FIG. 6, device 100 has the same geometry and features as device 100 of FIG. 2A. In this case, a first "U" shaped component 120a covers the left top surface 114a of the main body 110 and a second "U" shaped component 120b covers the right top surface 114a of the main body 110. The U-shaped components 120a, 120b are made of a soft, or flexible, or porous material. Examples of preferred materials for the U-shaped components 120a, 120b include silicone, latex, rigid and flexible polypropylene, cotton gauze, or some form of cotton or pressed paper molds. The U-shaped components 120a, 120b are designed to provide comfort during usage. There are also two openings 122a and 122b at the left and right portions 112a, 112b of the main body 110, respectively. These openings 122a, 122b are designed to provide added flexibility, especially if the material is more rigid.

Figure 7:
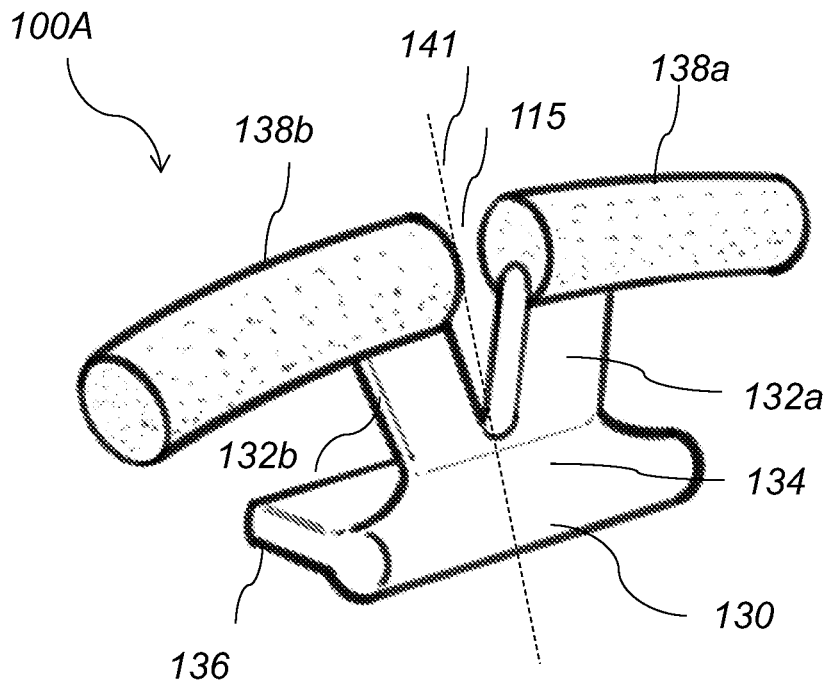
FIG. 7 is a perspective view of a sixth embodiment of the device for treating nosebleeds according to this invention.

Referring to FIG. 7, device 100A for treating nosebleeds includes a semi-rigid body 130 having a backwards extending bite tab 136, left and right portions 132a, 132b extending upwards from the top surface 134 of the body 130 and forming a V-shaped structure with a central gap 115. Device 100A also includes left and right cylindrical structures 138a, 138b extending horizontally and being attached to the top ends of the left and right portions 132a, 132b, respectively. Device 100A is shaped and dimensioned to be inserted into the buccal cavity of a user's 50 mouth and the cylindrical structures 138a, 138b are sized to conform and fit behind the user's upper lip and in front of the user's upper gums, as shown in FIG. 1A. The body 130 is shaped and dimensioned to be positioned in front of the user's upper front teeth and the bite tab 136 is shaped and dimensioned to provide a biting surface for the user's upper front teeth. Left and right cylindrical structures 138a, 138b extend horizontally from the inner sides of the top ends of the left and right portions 132a, 132b, respectively, and end beyond the left and right ends of the bite tab 136. Left and right cylindrical structures 138a, 138b curve downward from the midline to the left and right sides of the device, respectively. Left and right cylindrical structures 138a, 138b are made of a soft, flexible, or porous material. Examples of preferred materials for the left and right cylindrical structures 138a, 138b include silicone, latex, rigid and flexible polypropylene, cotton gauze, or some form of cotton or pressed paper molds. Gap 115 is shaped and dimensioned to fit around the user's frenulum, so that it does not interfere with the frenulum, which is located at the sagittal plane and top of the gum line.

Figure 8:
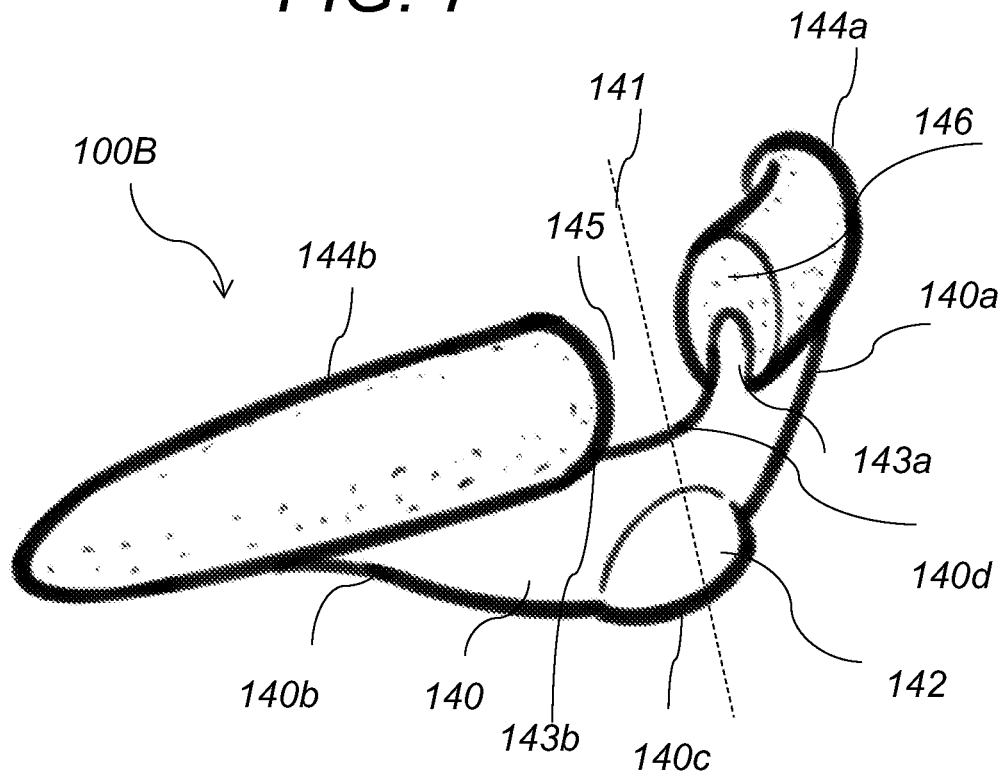
FIG. 8 is a perspective view of a seventh embodiment of the device for treating nosebleeds according to this invention.
Figure 9:
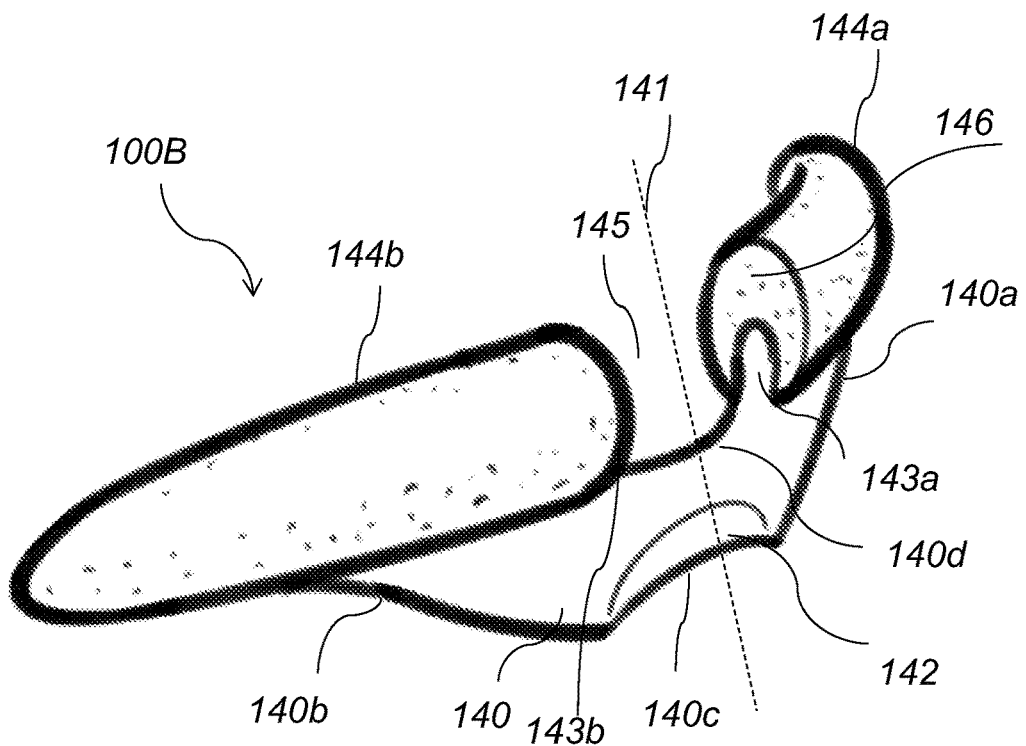
FIG. 9 is a perspective view of an eighth embodiment of the device for treating nosebleeds according to this invention.

Referring to FIG. 8 and FIG. 9, device 100B for treating nosebleeds includes a semi-rigid elongated body 140 that symmetrically curves inward from the midline 141 to the left and right sides 140a, 140b of the device. Elongated body 140 has a dome-shaped structure 142 formed at the middle bottom end 140c of body 140. Dome-shaped structure 142 is convex in FIG. 8 and concave in FIG. 9. Dome-shaped structure 142 provides a push surface for placing a user's tongue or finger and pushing the device upward in order to provide pressure to the nose. The top end 140d of body 140 includes a U-shaped cut 145 and left and right top ends 143a, 143b. U-shaped cut 145 is shaped and dimensioned to fit around the user's frenulum, so that it does not interfere with the frenulum. Left and right top ends 143a, 143b are covered with left and right conical structures 144a, 144b, respectively. Left and right conical structures 144a, 144b have oval shaped cross-sections 146 and extend from the inner sides of the top ends 143a, 143b respectively, and end beyond the left and right sides 140a, 140b of the elongated body 140, respectively. Conical structures 144a, 144b are sized to conform and fit behind the user's upper lip and in front of the user's upper gums. Semi-rigid elongated body 140 is made of silicone, latex, rigid and flexible polypropylene, cotton gauze, or some form of cotton or pressed paper molds. Left and right structures 144a, 144b are made of soft, flexible or porous material including silicone, latex, porous gauze, porous cotton, or porous pressed paper molds, among others.

Figure 10:
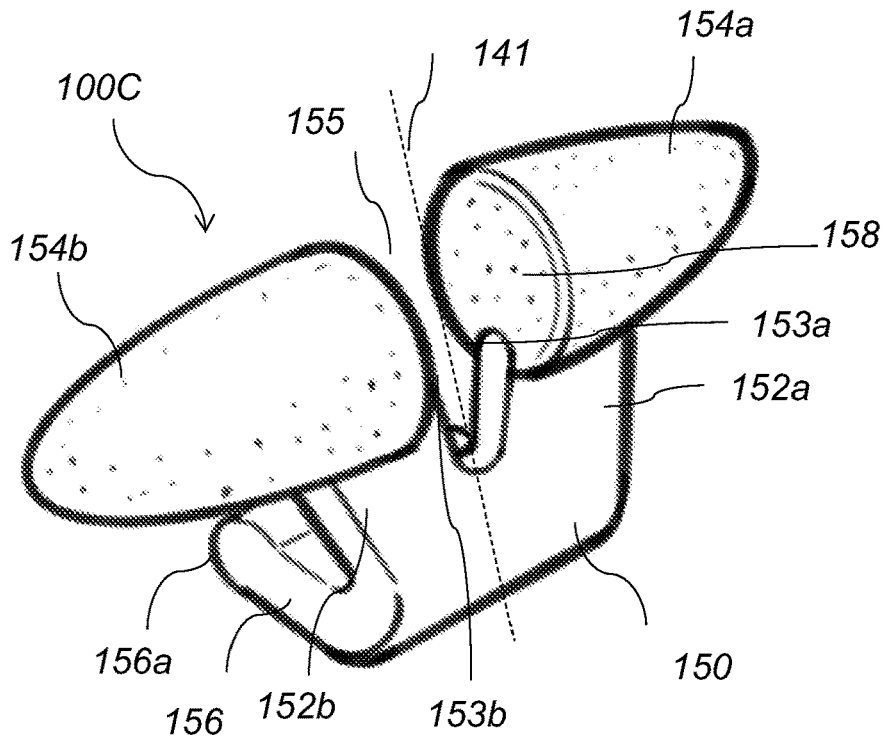
FIG. 10 is a perspective view of a ninth embodiment of the device for treating nosebleeds according to this invention.

Referring to FIG. 10, device 100C for treating nosebleeds includes a semi-rigid body 150 having a backwards extending bite tab 156, left and right portions 152a, 152b extending upwards from the top surface of the body 150 and forming a V-shaped structure with a central gap 155. Bite tab 156 extends backwards straight and terminates in a rounded end portion 156a. Device 100C also includes left and right conical structures 154a, 154b extending horizontally and being attached to the top ends of the left and right portions 153a, 153b, respectively. Device 100A is shaped and dimensioned to be inserted into the buccal cavity of a user's 50 mouth and the conical structures 154a, 154b are sized to conform and fit behind the user's upper lip and in front of the user's upper gums, as shown in FIG. 1A. The body 150 is shaped and dimensioned to be positioned in front of the user's upper front teeth and the bite tab 156 is shaped and dimensioned to provide a biting surface for the user's front teeth. Left and right conical structures 154a, 154b extend horizontally from the inner sides of the top ends of the left and right portions 153a, 153b, respectively, and end beyond the left and right ends of the bite tab 156. Left and right conical structures 154a, 154b have circular cross-sections 158. Semi-rigid body 150 is made of silicone, latex, rigid and flexible polypropylene, cotton gauze, or some form of cotton or pressed paper molds. Left and right structures 154a, 154b are made of soft, flexible or porous material including silicone, latex, porous gauze, porous cotton, or porous pressed paper molds, among others. Gap 155 is shaped and dimensioned to fit around the user's frenulum, so that it does not interfere with the frenulum, which is located at the sagittal plane and top of the gum line.

Figure 11:
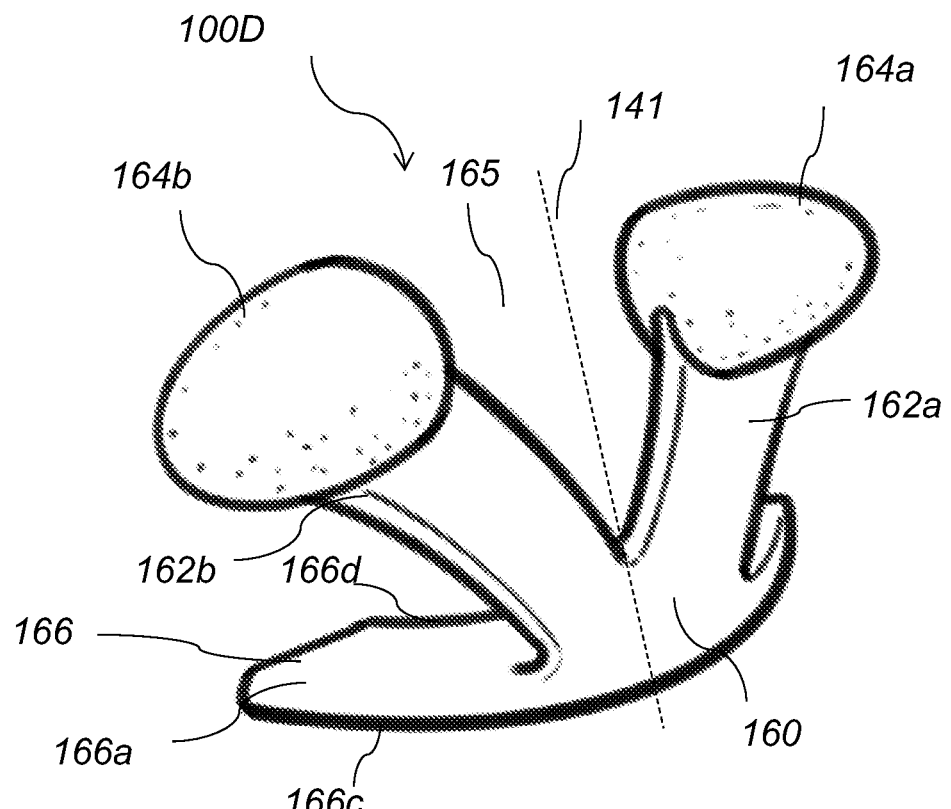
FIG. 11 is a perspective view of a tenth embodiment of the device for treating nosebleeds according to this invention.

Referring to FIG. 11, device 100D for treating nosebleeds includes a semi-rigid body 160 having a backwards extending bite tab 166, left and right portions 162a, 162b extending upwards from the top surface of the body 160 and forming a V-shaped structure with a central gap 165. Bite tab 166 has a flat top surface 166a and curved front 166c and back 166d edges. Edges 166c, 166d are curved to follow the alignment of the top teeth. Device 100D also includes left and right oval structures 164a, 164b extending horizontally and being attached to the top ends of the left and right portions 162a, 162b, respectively. Device 100D is shaped and dimensioned to be inserted into the buccal cavity of a user's 50 mouth and the oval structures 164a, 164b are sized to conform and fit behind the user's upper lip and in front of the user's upper gums, as shown in FIG. 1A. The body 160 is shaped and dimensioned to be positioned in front of the user's upper front teeth and the bite tab 166 is shaped and dimensioned to provide a biting surface for the user's front teeth. Left and right oval structures 164a, 164b extend horizontally from the inner sides of the top ends of the left and right portions 162a, 162b, respectively, and end beyond the left and right ends of the bite tab 166. Left and right oval structures 164a, 164b have circular cross-sections. Semi-rigid body 160 is made of silicone, latex, rigid and flexible polypropylene, cotton gauze, or some form of cotton or pressed paper molds. Left and right oval structures 164a, 164b are made of soft, flexible or porous material including silicone, latex, porous gauze, porous cotton, or porous pressed paper molds, among others. Gap 165 is shaped and dimensioned to fit around the user's frenulum, so that it does not interfere with the frenulum, which is located at the sagittal plane and top of the gum line.

Figure 12:
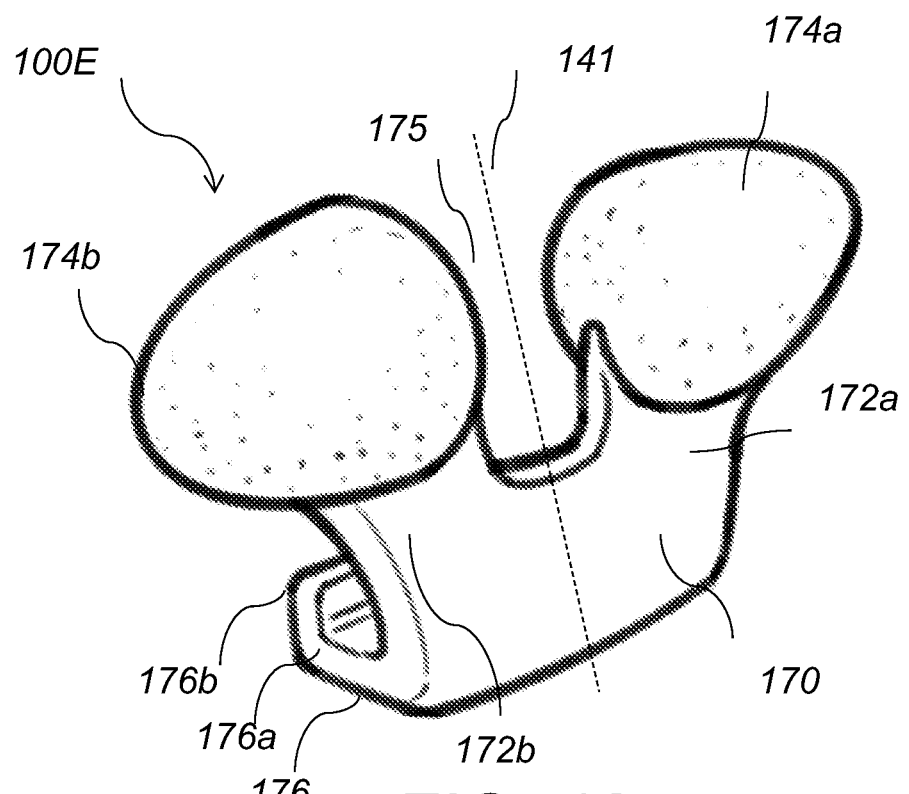
FIG. 12 is a perspective view of an eleventh embodiment of the device for treating nosebleeds according to this invention.
Figure 13E:
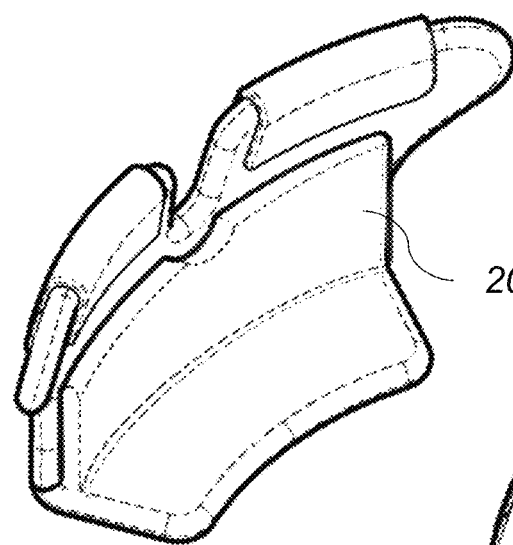
FIG. 13E is a back perspective view of the embodiment of the device for treating nosebleeds of FIG. 13A.
Figure 13F:
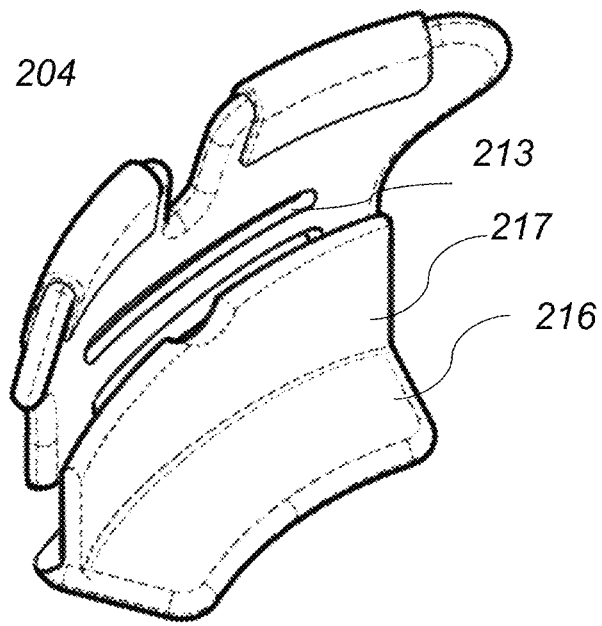
FIG. 13F is a back perspective view of the embodiment of the device for treating nosebleeds of FIG. 13A with the bite tab moved down.
Figure 13G:
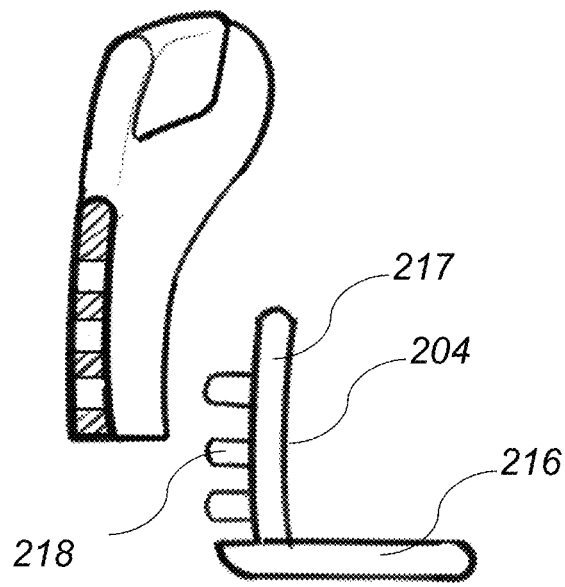
FIG. 13G is a side cross-sectional view of the embodiment of the device for treating nosebleeds of FIG. 13A with the bite tab being disengaged from the main body.
Figure 14A:
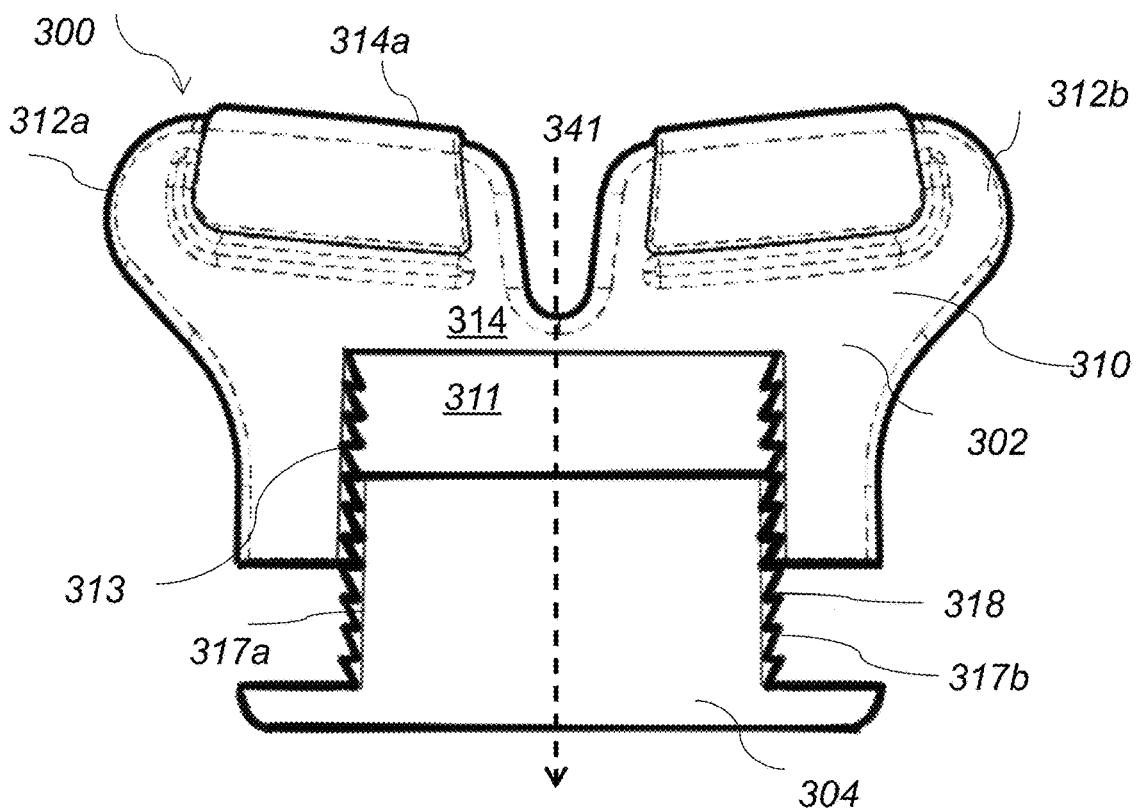
FIG. 14A is a front view of another embodiment of the device for treating nosebleeds according to this invention.
Figure 14B:
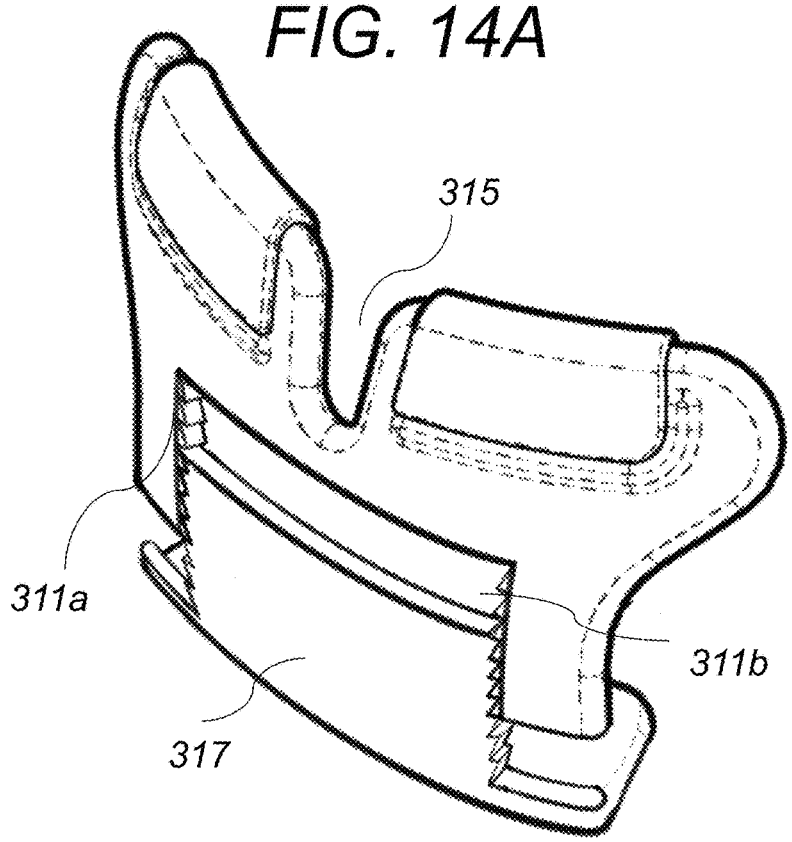
FIG. 14B is a front perspective view of the embodiment of the device for treating nosebleeds of FIG. 14A.
Figure 14C:
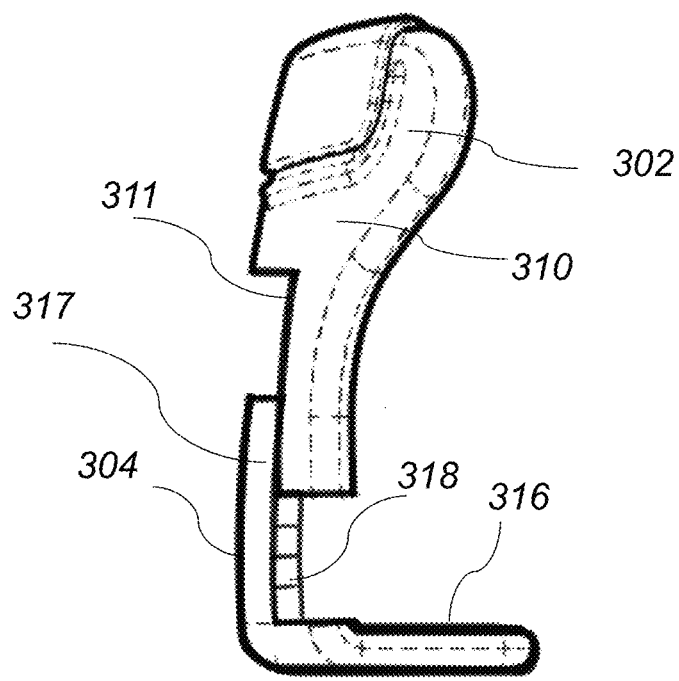
FIG. 14C is a side view of the embodiment of the device for treating nosebleeds of FIG. 14A.
Figure 14D:
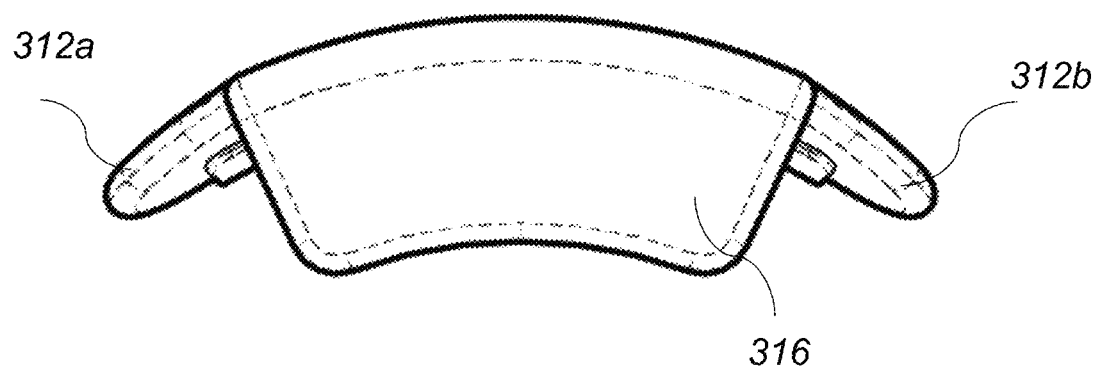
FIG. 14D is a bottom view of the embodiment of the device for treating nosebleeds of FIG. 14A.
Figure 15A:
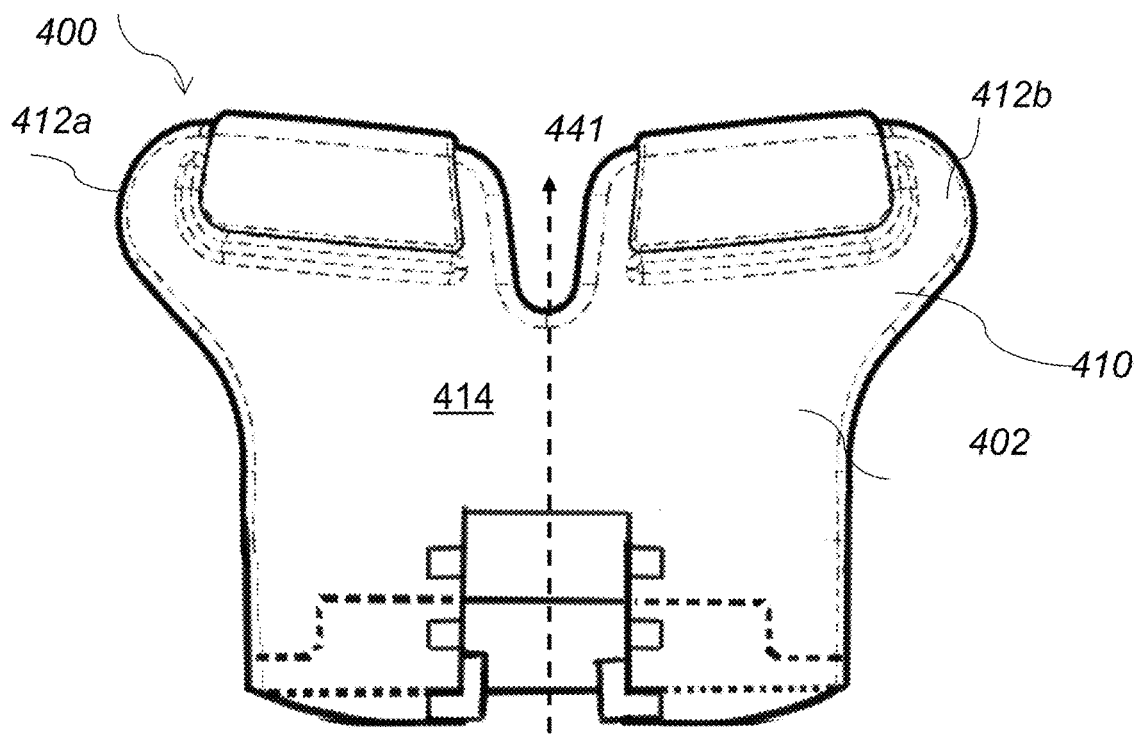
FIG. 15A is a front view of another embodiment of the device for treating nosebleeds according to this invention.
Figure 15B:
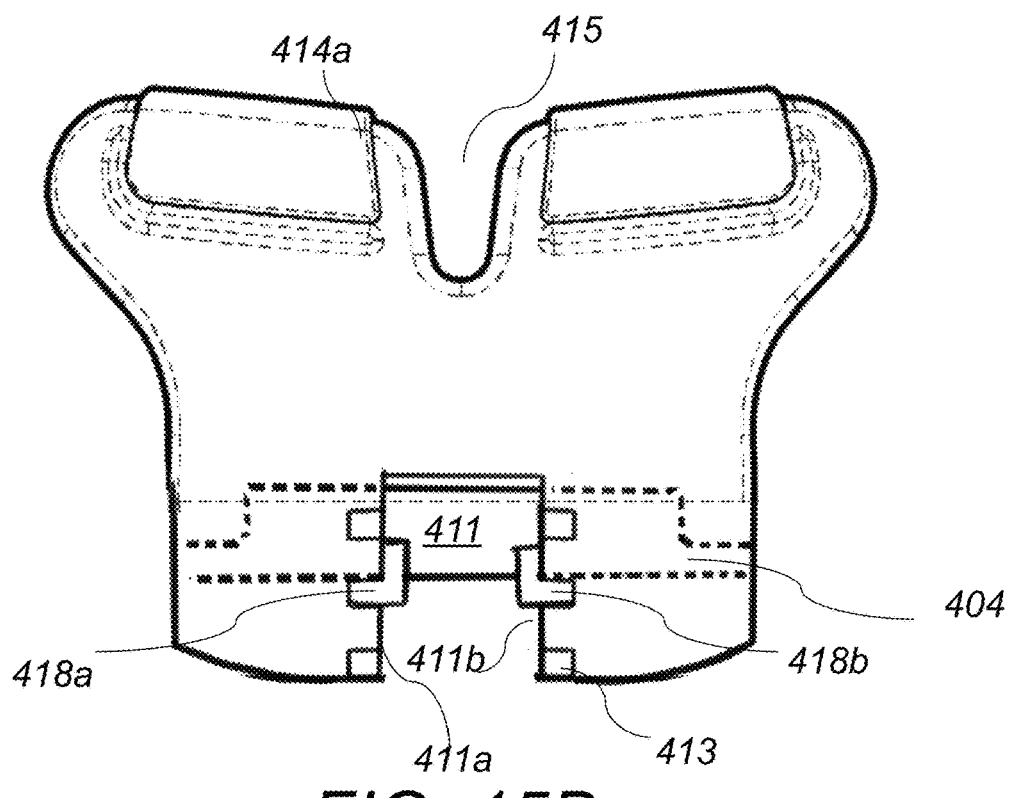
FIG. 15B is a front view of the embodiment of the device for treating nosebleeds of FIG. 15A with the bite tab moved up.
Figure 15D:
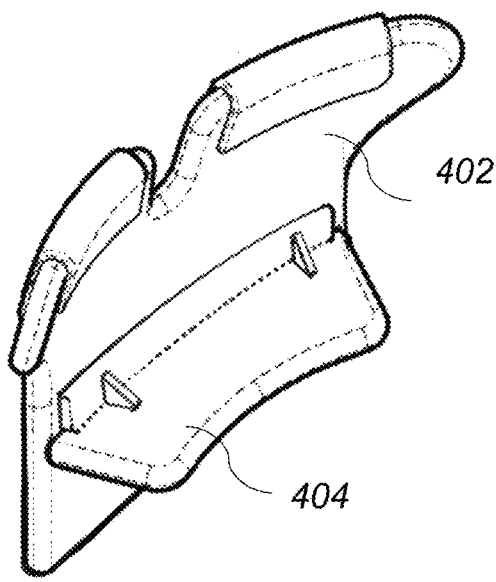
FIG. 15D is a back perspective view of the embodiment of the device for treating nosebleeds of FIG. 15A with the bite tab moved up.
Figure 15C:
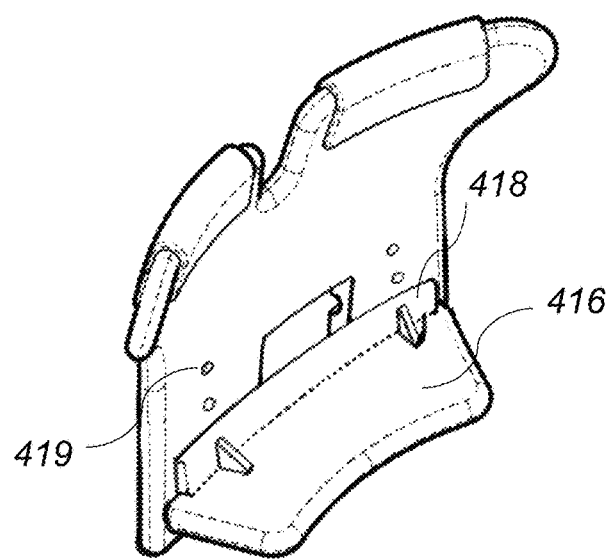
FIG. 15C is a back perspective view of the embodiment of the device for treating nosebleeds of FIG. 15A.
Figure 15E:
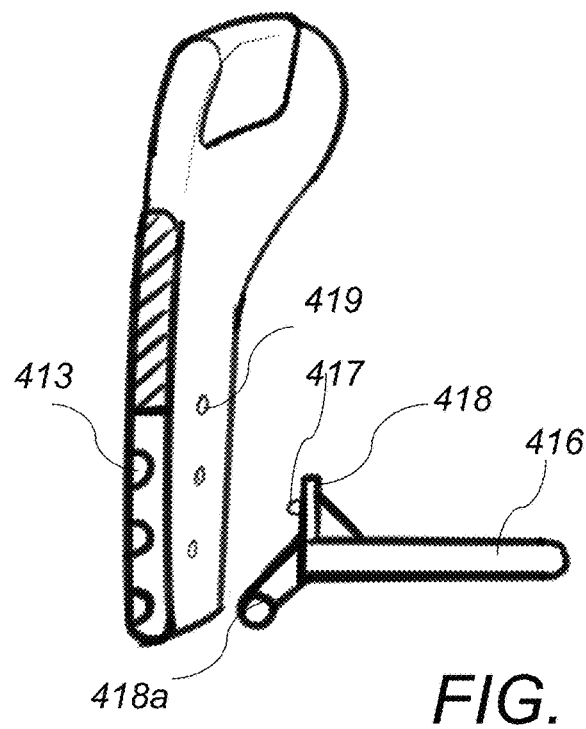
FIG. 15E is a side cross-sectional view of the embodiment of the device for treating nosebleeds of FIG. 15A with the bite tab being disengaged from the main body.
Figure 16A:
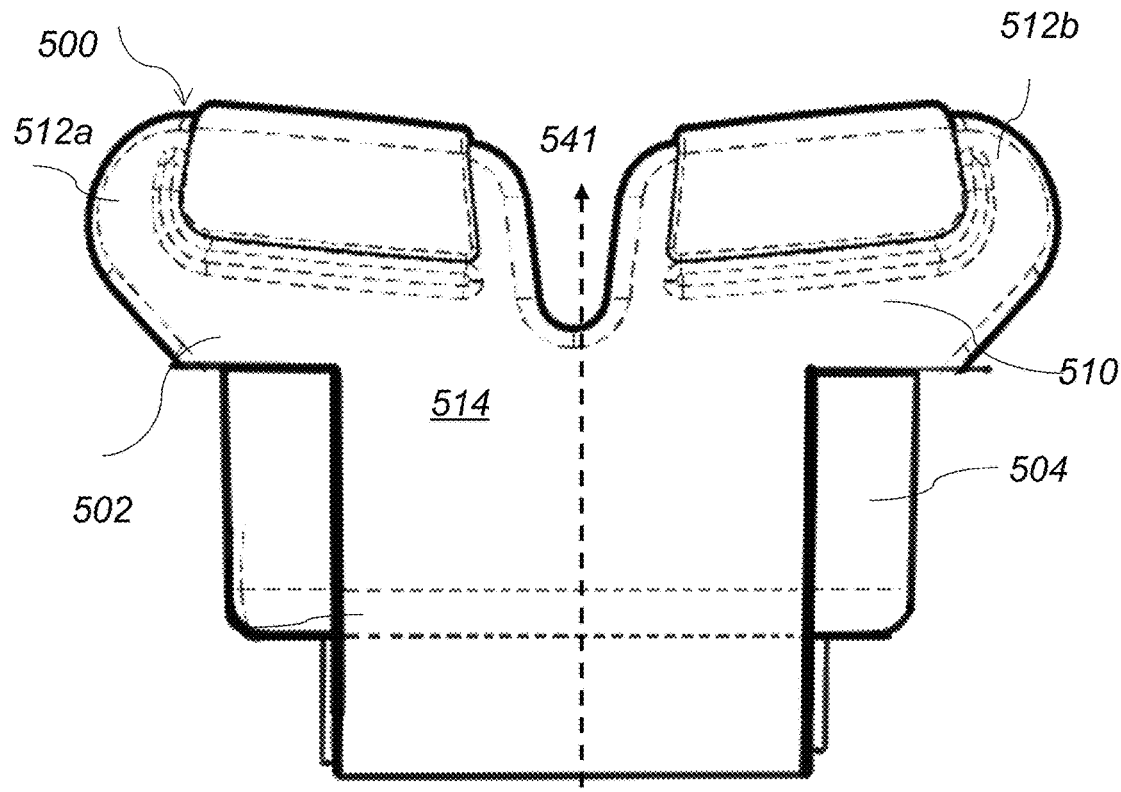
FIG. 16A is a front view of another embodiment of the device for treating nosebleeds according to this invention.
Figure 16B:
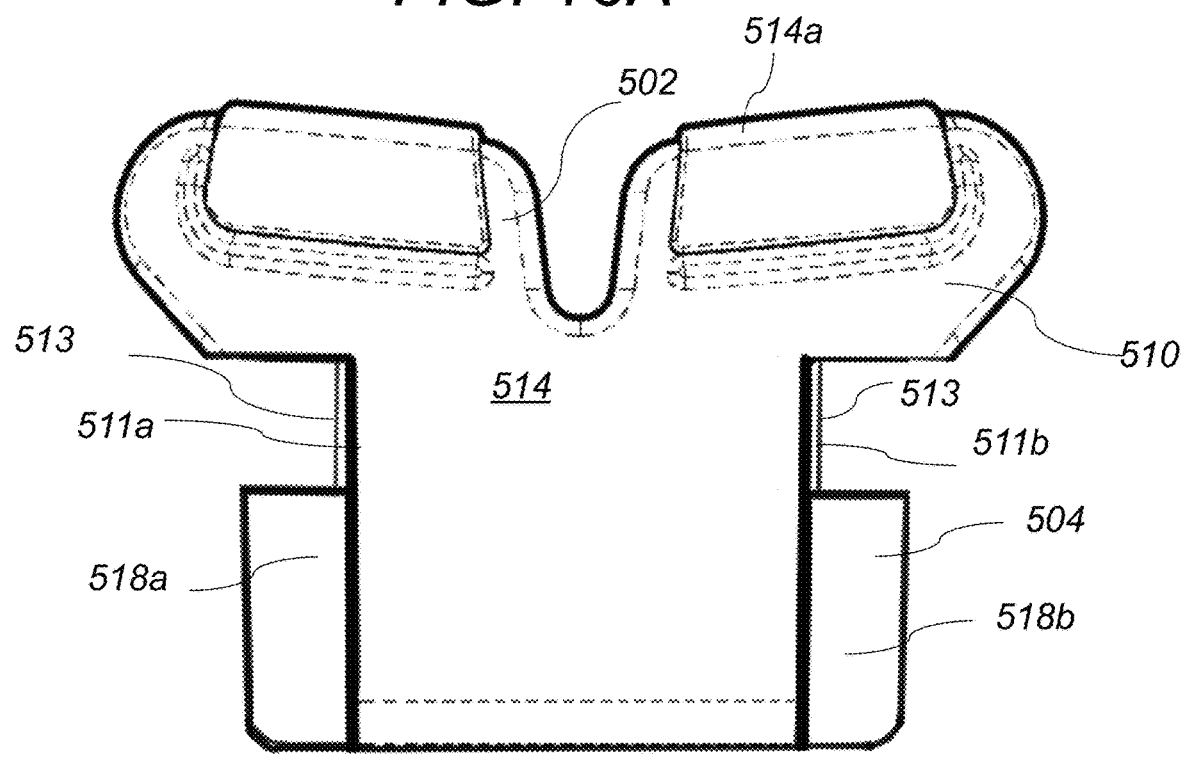
FIG. 16B is a front view of the embodiment of the device for treating nosebleeds of FIG. 16A with the bite tab moved up.
Figures 16C, 16D:
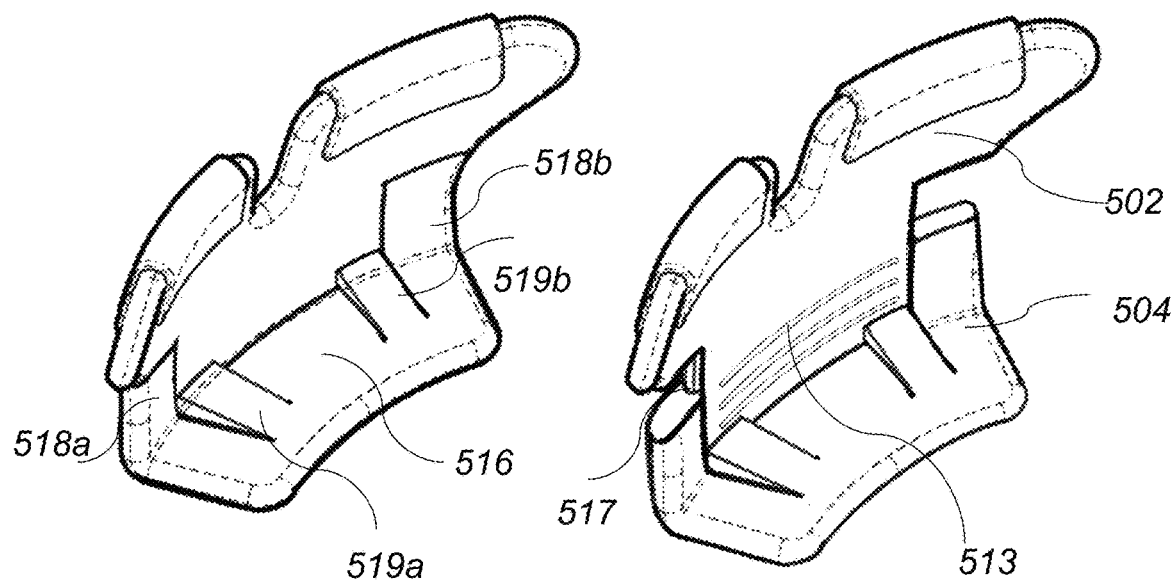
FIG. 16C is a back perspective view of the embodiment of the device for treating nosebleeds of FIG. 16A.
FIG. 16D is a back perspective view of the embodiment of the device for treating nosebleeds of FIG. 16A with the bite tab moved up.
Figure 16F:
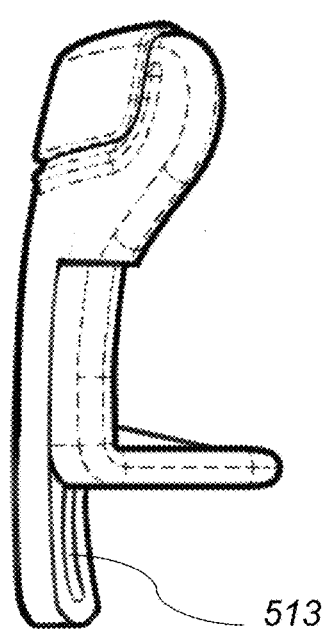
FIG. 16F is a side view of the embodiment of the device for treating nosebleeds of FIG. 16A with the bite tab moved up.
Figure 16E:
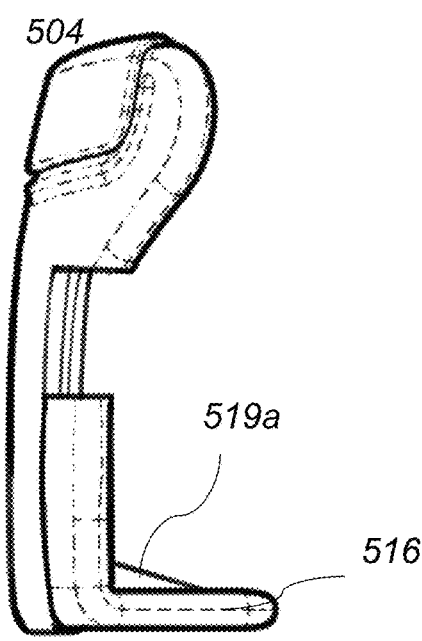
FIG. 16E is a side view of the embodiment of the device for treating nosebleeds of FIG. 16A.
Figure 17A:
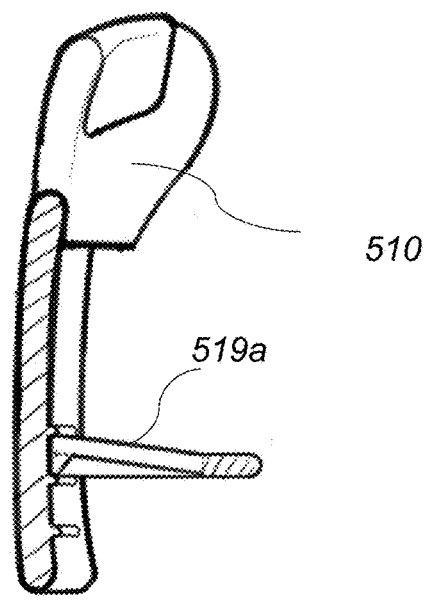
FIG. 17A is a partially cross-sectional side view of the embodiment of the device for treating nosebleeds of FIG. 16A.
Figures 17B, 17C, 17D:
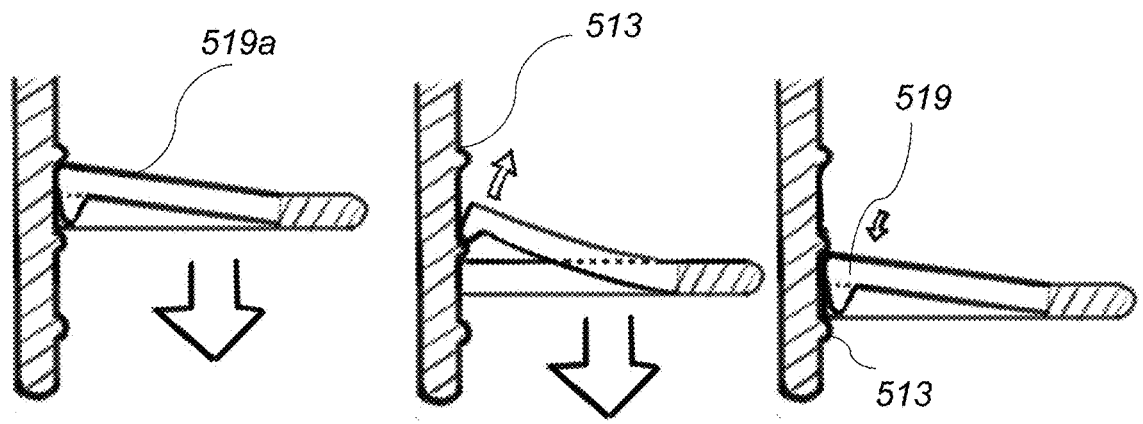
FIG. 17B, FIG. 17C and FIG. 17D depict a portion of the cross-sectional side view of the embodiment of the device for treating nosebleeds of FIG. 16A in various stages of engaging the bite tab with the main body.

Referring to FIG. 12, device 100E for treating nosebleeds includes a semi-rigid body 170 having a backwards extending bite tab 176, left and right portions 172a, 172b extending upwards from the top surface of the body 170 and forming a U-shaped structure with a central gap 175. Bite tab 176 has a flat top surface 176a and the back edge 176b is curved upwards by 90 degrees relative to the top surface 176a, forming a J-hook that is configured to wrap around the user's top front teeth. Edge 176b extends upwards above the top surface 176a by a height in the range of ⅛ to ¼ inch. Device 100E also includes left and right oval structures 174a, 174b extending horizontally and being attached to the top ends of the left and right portions 172a, 172b, respectively. Device 100E is shaped and dimensioned to be inserted into the buccal cavity of a user's 50 mouth and the oval structures 174a, 174b are sized to conform and fit behind the user's upper lip and in front of the user's upper gums, as shown in FIG. 1A. The body 170 is shaped and dimensioned to be positioned in front of the user's upper front teeth and the bite tab 176 is shaped and dimensioned to provide a biting surface for the user's upper front teeth. Left and right oval structures 174a, 174b extend horizontally from the inner sides of the top ends of the left and right portions 172a, 172b, respectively, and end beyond the left and right ends of the bite tab 176. Left and right oval structures 174a, 174b have circular cross-sections. Semi-rigid elongated body 170 is made of silicone, latex, rigid and flexible polypropylene, cotton gauze, or some form of cotton or pressed paper molds. Left and right oval structures 174a, 174b are made of soft, flexible or porous material including silicone, latex, porous gauze, porous cotton, or porous pressed paper molds, among others. Gap 175 is shaped and dimensioned to fit around the user's frenulum, so that it does not interfere with the frenulum, which is located at the sagittal plane and top of the gum line.

Referring to FIG. 13A-FIG. 13G, a device 200 for treating nosebleeds includes a main body 202 and a separate bite tab 204. Bite tab 204 removably engages the main body 202 and is configured to move up and down along 205 in order to adjust the height of the device 200, so that it can fit in the mouths of both adults and children. Main body 202 includes an elongated body 210, shaped and dimensioned to be inserted into the buccal cavity of a user's 50 mouth and to fit behind the user's upper lip and in front of the user's upper gums, as shown in FIG. 1A. The top portion of body 210 includes a gap 215 extending along the midline 241. Gap 215 has a V-shape and is dimensioned to fit around the user's frenulum, without interfering with the frenulum, which is located at the sagittal plane and top of the gum line. Elongated body 210 includes a central portion 214 having a top 214a, a bottom 214b and left and right portions 212a, 212b that extend sidewise from the central portion 214. Top 214a, is curved and together with the central portion 214 curves backwards and has a curvature radius that matches the radius of the user's upper gum line. Bottom 214b extends straight downward from the body 210. The central portion 214 includes three horizontal cutouts (slots) 213. Bite tab 204 includes a horizontally extending portion 216 and a vertically extending portion 217. The vertically extending portion 217 includes three horizontally extending protrusions (ribs) 218 that are shaped and dimensioned to fit within and engage the slots 213 of the main body 202. The vertically extending portion 217 is placed behind the main body 202 and the horizontally extending protrusions 218 are inserted into the slots 213 to lock the position of the bite tab 204 relative to the main body 202. The height of the device 200 is adjusted by moving the bite tab 204 up or down relative to the main body 202 and locking its position by inserting protrusions 218 into higher or lower positioned slots 213, respectively. The central portion 214 of the main body 202 is shaped and dimensioned to be positioned in front of the user's upper front teeth and the horizontally extending portion 216 of the movable bite tab 204 is shaped and dimensioned to provide a biting surface for the user's upper front teeth. Left and right portions 212a, 212b of the main body 202 are shaped and dimensioned to fit the user's left and right sides of the upper gums, respectively.

In operation, the user 50 inserts the device 200 in the mouth and places the elongated body 210 behind the upper lip and in front of the top gums. Next, the user bites down on the horizontally extending portion 216 of the bite tab 204 and the biting action causes the top 214a and the central portion 214 to apply pressure upward towards the anterior portion of the nose. The applied pressure blocks the blood flow to the nose and the anterior arteries and causes device 200 to act as a tourniquet that reduces and stops nosebleeds.

Referring to FIG. 14A-FIG. 14D, a device 300 for treating nosebleeds includes a main body 302 and a separate bite tab 304. Bite tab 304 removably engages the main body 302 and is configured to move down along 341 in order to adjust the height of the device 300, so that it can fit in the mouths of both adults and children. Main body 302 includes an elongated body 310, shaped and dimensioned to be inserted into the buccal cavity of a user's 50 mouth and to fit behind the user's upper lip and in front of the user's upper gums, as shown in FIG. 1A. The top portion of body 310 includes a gap 315 extending along the midline 341. Gap 315 has a V-shape and is dimensioned to fit around the user's frenulum, without interfering with the frenulum, which is located at the sagittal plane and top of the gum line. Elongated body 310 includes a central portion 314 having a top 314a, and left and right portions 312a, 312b that extend sidewise from the central portion 314. Top 314a, is curved and together with the central portion 314 curves backwards and has a curvature radius that matches the radius of the user's upper gum line. The bottom of central portion 314 includes a rectangular cutout 311. Rectangular cutout has sides 311a, 311b that include a series of teeth 313. Teeth 313 have a flat portion that is horizontal. Bite tab 304 includes a horizontally extending portion 316 and a vertically extending portion 317. The vertically extending portion 317 is shaped and sized to fit within the cutout 311 of the main body 302. The left and right sides 317a, 317b of the vertically extending portion 317 include teeth 318 that are shaped and sized to engage the teeth 313 of the main body 302. The vertically extending portion 317 is placed within the cutout 311 and teeth 318 engage the teeth 313 of the cutout 311 to lock the position of the bite tab 304 relative to the main body 302. The height of the device 300 is adjusted by moving the bite tab 304 down relative to the main body 302. The horizontal portion of teeth 313 prevent the upward motion of the bite tab 304, while in use. The central portion 314 of the main body 302 is shaped and sized to be positioned in front of the user's upper front teeth and the horizontally extending portion 316 of the bite tab 304 is shaped and sized to provide a biting surface for the user's upper front teeth. Left and right portions 312a, 312b of the main body 302 are shaped and sized to fit the user's left and right sides of the upper gums, respectively.

Referring to FIG. 15A-FIG. 15E, a device 400 for treating nosebleeds includes a main body 402 and a separate bite tab 404. Bite tab 404 removably engages the main body 402 and is configured to move up along 441 in order to adjust the height of the device 400, so that it can fit in the mouths of both adults and children. Main body 402 includes an elongated body 410, shaped and sized to be inserted into the buccal cavity of a user's 50 mouth and to fit behind the user's upper lip and in front of the user's upper gums, as shown in FIG. 1A. The top portion of body 410 includes a gap 415 extending along the midline 441. Gap 415 has a V-shape and is dimensioned to fit around the user's frenulum, without interfering with the frenulum, which is located at the sagittal plane and top of the gum line. Elongated body 410 includes a central portion 414 having a top 414a, and left and right portions 412a, 412b that extend sidewise from the central portion 414. Top 414a, is curved and together with the central portion 414 curves backwards and has a curvature radius that matches the radius of the user's upper gum line. The bottom of central portion 414 includes a rectangular cutout 411 in the middle of the device. Rectangular cutout 411 has sides 411a, 411b that include notches 413 that do not cut all the way through the device. Bite tab 404 includes a horizontally extending portion 416, a vertically extending portion 418, and left and right finger extensions 418a, 418b that protrude forward and downward at an angle. Each finger extension 418a, 418b has a dowel bent at 90° degrees horizontally from the finger and the dowels of finger extensions 418a, 418b extend in opposite directions to each other. The dowels of finger extensions 418a, 418b are sized and shaped to fit within the notches 413 of the main body 402. The vertically extending portion 418 includes small pin dowels 417 that are shaped and sized to fit into pin openings 419 formed on the backside of the main body 402. The height of the device 400 is adjusted by moving the bite tab 404 up relative to the main body 402. The bite tab 404 is pivoted downward about the finger dowels 418a, 418b to clear the pin dowel openings 419 and the finger dowels 418a, 418b are pushed out of the notches 413 and placed in another set of notches. The pin dowels 417 are then placed into corresponding pin dowel openings 419 of the main body to set the bite tab 404 at a different height relative to the main body 402.

Referring to FIG. 16A-FIG. 17D, a device 500 for treating nosebleeds includes a main body 502 and a separate bite tab 504. Bite tab 504 removably engages the main body 502 and is configured to move up along 541 in order to adjust the height of the device 500, so that it can fit in the mouths of both adults and children. Main body 502 includes an elongated body 510, shaped and sized to be inserted into the buccal cavity of a user's 50 mouth and to fit behind the user's upper lip and in front of the user's upper gums, as shown in FIG. 1A. The top portion of body 510 includes a gap 515 extending along the midline 541. Gap 515 has a V-shape and is dimensioned to fit around the user's frenulum, without interfering with the frenulum, which is located at the sagittal plane and top of the gum line. Elongated body 510 includes a central portion 514 having a top 514a, and left and right portions 512a, 512b that extend sidewise from the central portion 514. Top 514a, is curved and together with the central portion 514 curves backwards and has a curvature radius that matches the radius of the user's upper gum line. Central portion 514 includes left and right side cutouts 511a, 511b and each side cutout has a rib track 513. The back side of the central portion 514 includes three horizontal protruding ribs 513. Bite tab 504 includes a horizontally extending portion 516, left and right vertically extending portions 518a, 518b, and one or two pawls 519a, 519b. The vertically extending portions 518a, 518b of the bite tab 504 include rib grooves 517 that are shaped and sized to slidably engage the rib tracks 513 on the side cutouts 511a, 511b of the main body 502. Pawls 519a, 519b extend from the horizontally extending portion 516 of the bite tab 504 and are angled upwardly. Each pawl 519a, 519b includes a head 519 with a triangular cross-section that is shaped to engage the protruding ribs 513 on the back side of the main body 502. The height of the device 500 is adjusted by moving the bite tab 504 down relative to the main body 502. When the bite tab 504 is pushed down the pawls 519a, 519b are flexed upward giving clearance for the bite tab to slide downward to the next position. Once the pawl head 519 passes the rib 513 of the main body, the pawl 519a snaps back down and rests down on the next rib 513. When the user pushes the bite tab 504 upwards, the pawls 519a, 519b are influenced by the rib 513 to angle downward and this action prevents movement of the bite tab 504 relative to the main body 502.

Figure 18A:
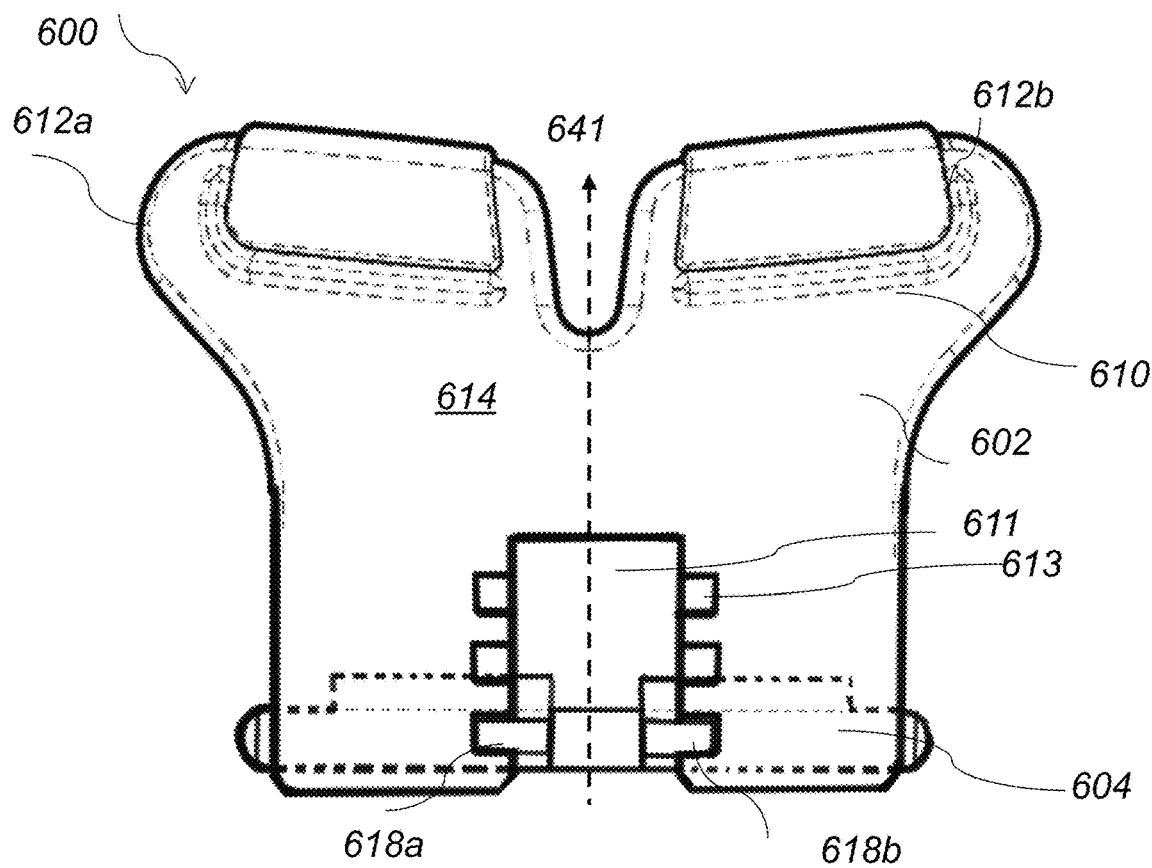
FIG. 18A is a front view of another embodiment of the device for treating nosebleeds according to this invention.
Figure 18B:
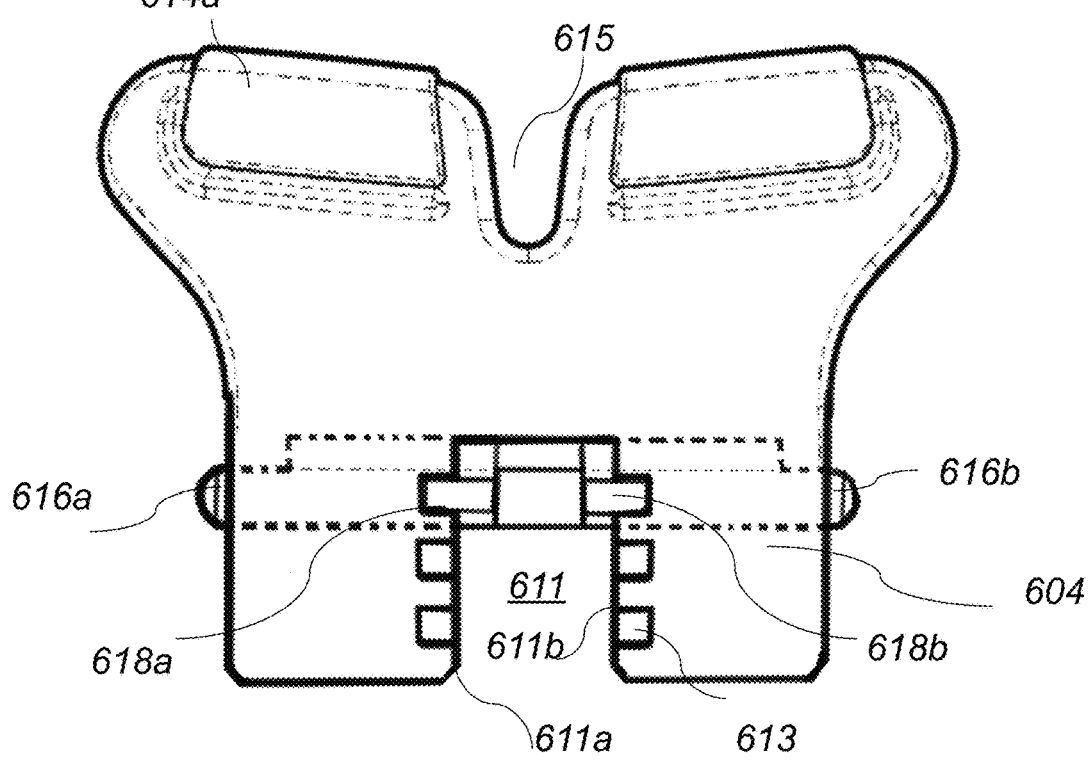
FIG. 18B is a front view of the embodiment of the device for treating nosebleeds of FIG. 18A with the bite tab moved up.
Figures 18C, 18D:
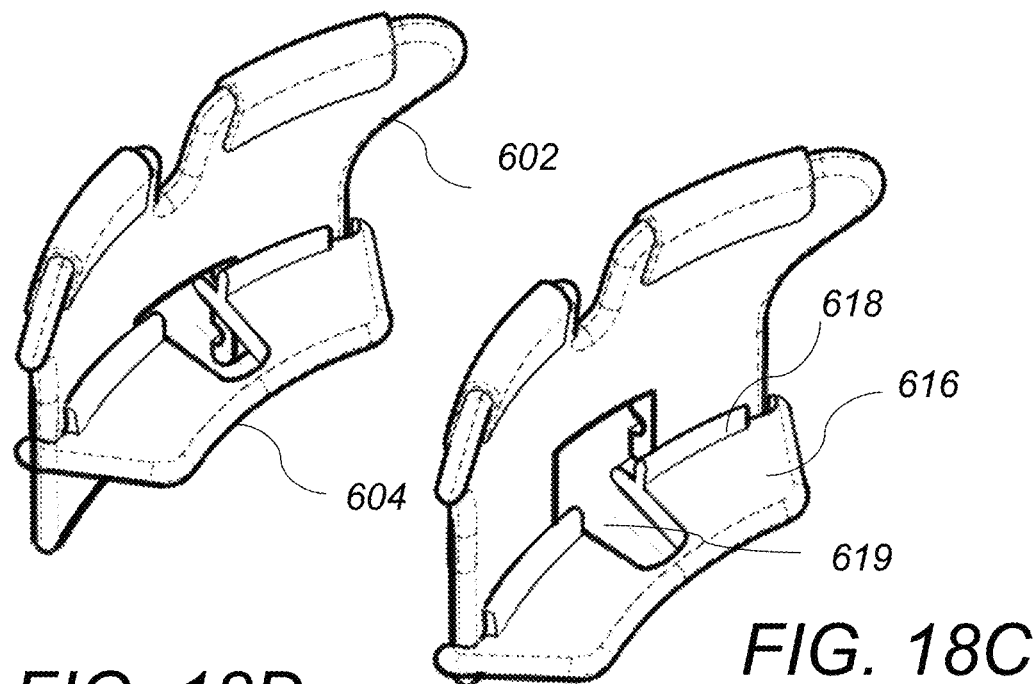
FIG. 18C is a back perspective view of the embodiment of the device for treating nosebleeds of FIG. 18A.
FIG. 18D is a back perspective view of the embodiment of the device for treating nosebleeds of FIG. 18A with the bite tab moved up.
Figures 18E, 18F:
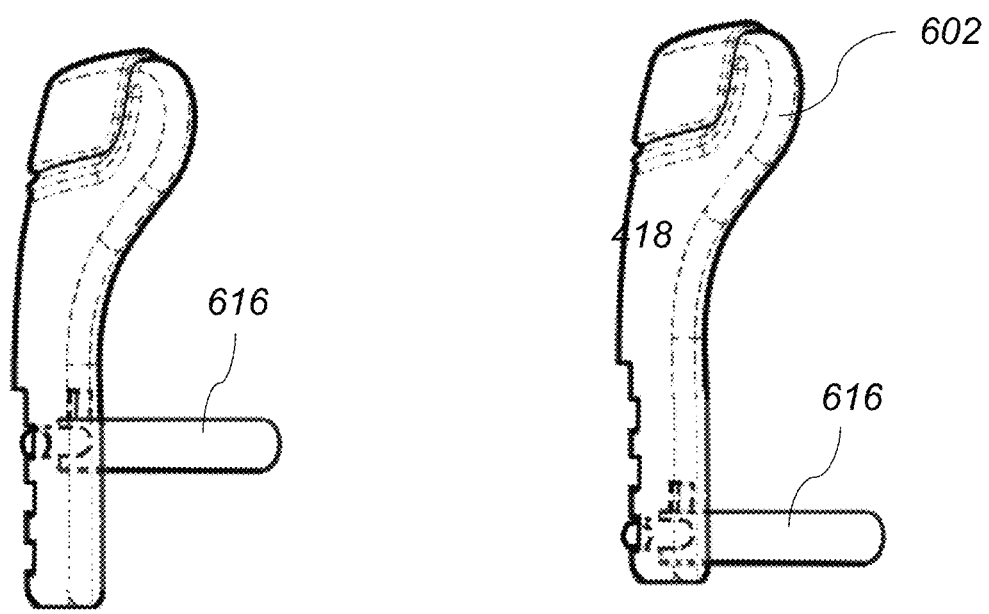
FIG. 18E is a side view of the embodiment of the device for treating nosebleeds of FIG. 18A.
FIG. 18F is a side view of the embodiment of the device for treating nosebleeds of FIG. 18A with the bite tab moved up.
Figure 18G:
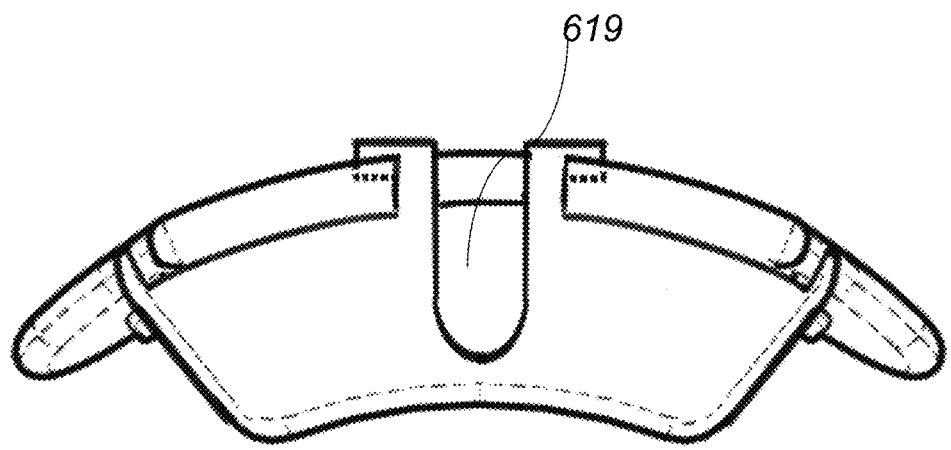
FIG. 18G is a bottom view of the embodiment of the device for treating nosebleeds of FIG. 18A.
Figure 18H:
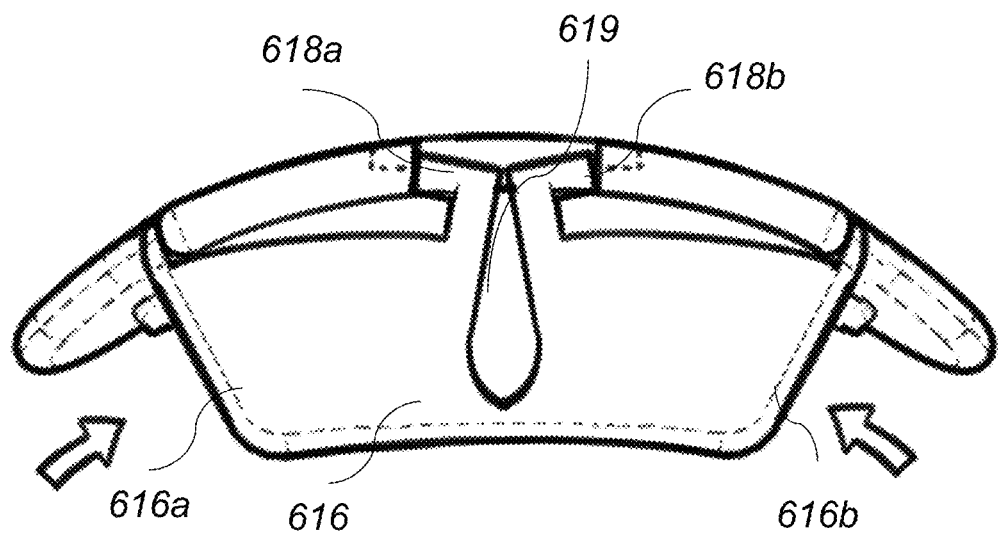
FIG. 18H is a bottom view of the embodiment of the device for treating nosebleeds of FIG. 18A with the bite tab edges pushed inward.

Referring to FIG. 18A-FIG. 18H, a device 600 for treating nosebleeds includes a main body 602 and a separate bite tab 604. Bite tab 604 removably engages the main body 602 and is configured to move up along 641 in order to adjust the height of the device 600, so that it can fit in the mouths of both adults and children. Main body 602 includes an elongated body 610, shaped and sized to be inserted into the buccal cavity of a user's 50 mouth and to fit behind the user's upper lip and in front of the user's upper gums, as shown in FIG. 1A. The top portion of body 610 includes a gap 615 extending along the midline 641. Gap 615 has a V-shape and is dimensioned to fit around the user's frenulum, without interfering with the frenulum, which is located at the sagittal plane and top of the gum line. Elongated body 610 includes a central portion 614 having a top 614a, and left and right portions 612a, 612b that extend sidewise from the central portion 614. Top 614a, is curved and together with the central portion 614 curves backwards and has a curvature radius that matches the radius of the user's upper gum line. The bottom of central portion 614 includes a rectangular cutout 611 in the middle of the device. Rectangular cutout 611 has sides 611a, 611b that include notches 613 that do not cut all the way through the device. Bite tab 604 includes a horizontally extending portion 616, a vertically extending portion 618, a center cutout 619, left and right finger extensions 618a, 618b that protrude forward from the inner edges of the center cutout 619 and extend downward at an angle, and outer extensions 616a, 616b that protrude forward from the front of the horizontally extending portion 616 and are placed around the left and right edges of the main body 602, respectively. Vertically extending portion 618 is placed behind the main body 602. Each finger extension 618a, 618b has a dowel bent at 90° degrees horizontally from the finger and the dowels of finger extensions 618a, 618b extend in opposite directions to each other. The dowels of finger extensions 618a, 618b are sized and shaped to fit within the notches 613 of the main body 602. The height of the device 600 is adjusted by moving the bite tab 604 up or down relative to the main body 602. The user squeezes the outside edges 616a, 616b of the bite tab 604 inward, resulting in bending the bite tab 604 and clearing the finger extensions 618a, 618b from the notches 613, as shown in FIG. 18H. Next, the user moves the bite tab 604 up or down to the desired height, releases the pinch, resulting in inserting the finger extensions 618a, 618b into another set of notches 613 and locks the bite tab 604 into the new position.

Several embodiments of the present invention have been described. Nevertheless, it will be understood that various modifications may be made without departing from the spirit and scope of the invention. Accordingly, other embodiments are within the scope of the following claims.

What is claimed is:

1. A device for treating nosebleeds comprising:
a mouth insert comprising a main body and a bite tab, wherein the bite tab removably engages the main body and is configured to move up and/or down vertically in order to adjust the height of the device;
wherein the main body comprises a horizontally extending elongated portion, a center portion extending downward from a bottom surface of the elongated portion, wherein the center portion comprises a narrower width than the horizontally extending elongated portion;
wherein the elongated portion of the main body is shaped and dimensioned to be inserted into a buccal cavity of a user's mouth and to fit behind an upper lip of the user and in front of the upper gums of the user, and wherein the center portion is shaped and dimensioned to be positioned only in front of upper front teeth of the user; and
wherein the bite tab comprises a horizontally extending portion and a vertically extending portion and wherein the vertically extending portion is configured to removably engage the center portion of the main body and wherein the horizontally extending portion comprises a push-surface used for pushing the device upward in order to provide pressure to the user's nose.

2. The device of claim 1, wherein the vertically extending portion of the bite tab comprises protrusions that are shaped and sized to fit within and engage slots formed on the center portion of the main body.

3. The device of claim 1, wherein the vertically extending portion of the bite tab is shaped and sized to fit within a cutout opening formed on the center portion of the main body.

4. The device of claim 3, wherein the vertically extending portion of the bite tab comprises teeth on a left side and a right side and wherein the teeth of the vertically extending portion are shaped and sized to engage teeth formed on a left side and a right side of the cutout opening of the center portion of the main body, respectively.

5. The device of claim 4, wherein the teeth of the vertically extending portion comprise a flat and horizontal portion that prevents upward motion of the bite tab while in use.

6. The device of claim 1, wherein the bite tab further comprises left and right finger extensions that are shaped and sized to fit within and engage notches formed on a left side and a right side of a cutout opening of the center portion of the main body, respectively.

7. The device of claim 6, wherein each finger extension protrudes forward and downward at an angle and comprises a dowel bent at 90° degrees.

8. The device of claim 1, wherein the vertically extending portion of the bite tab comprises pin dowels that are shaped and sized to fit into pin openings formed on the center portion of the main body.

9. The device of claim 1, wherein the vertically extending portion of the bite tab comprises a left component and a right component that are shaped and sized to fit within a left cutout opening and a right cutout opening formed on the left side and the right side of the center portion of the main body, respectively.

10. The device of claim 9, wherein the left and right components of the vertically extending portion of the bite tab comprise rib grooves that are shaped and sized to engage rib tracks formed on the left cutout opening and the right cutout opening of the center portion of the main body, respectively.

11. The device of claim 9, wherein the bite tab further comprises a pawl extending from the horizontally extending portion of the bite tab and being angled upwardly, and wherein the pawl comprises a pawl head shaped and sized to engage a protrusion on the center portion of the main body.

12. The device of claim 1, wherein the bite tab further comprises a center cutout in the horizontally extending portion and left and right finger extensions protruding from left and right edges of the center cutout of the bite tab, and wherein the left and right finger extensions are shaped and sized to fit within and engage left and right notches formed on left and right sides of a center cutout of the center portion of the main body.

13. The device of claim 1, wherein the bite tab further comprises left and right outer extensions protruding forward from the horizontally extending portion of the bite tab and wherein the left and right outer extensions are shaped and sized to be placed around left and right sides of the center portion of the main body.

14. The device of claim 1, wherein the elongated portion of the main body comprises a U-shaped gap dimensioned to fit around a frenulum of the user.

15. The device of claim 1, wherein the elongated portion of the main body and the center portion are curved backwards and have a curvature radius that matches the user's upper gum line radius.

16. The device of claim 1, wherein the elongated portion of the main body comprises an adjustable width.

17. The device of claim 16, wherein the elongated portion of the main body comprises cut-away features on left and right sides of the elongated portion and wherein the cut-away features are designed to tear off and thereby to reduce the width of the device.

18. The device of claim 16, wherein the elongated portion of the main body comprises foldable extensions on left and right sides of the elongated portion and wherein the foldable extensions are designed to unfold and thereby to increase the width of the device.

19. A method for treating nosebleeds comprising:
providing a mouth insert comprising a main body and a bite tab, wherein the bite tab removably engages the main body and is configured to move up and/or down vertically in order to adjust the height of the device; wherein the main body comprises a horizontally extending elongated portion, a center portion extending downward from a bottom surface of the elongated portion, wherein the center portion comprises a narrower width than the horizontally extending elongated portion; wherein the elongated portion of the main body is shaped and dimensioned to be inserted into a buccal cavity of a user's mouth and to fit behind an upper lip of the user and in front of upper gums of the user, and wherein the center portion is shaped and dimensioned to be positioned only in front of upper front teeth of the user; wherein the bite tab comprises a horizontally extending portion and a vertically extending portion and wherein the vertically extending portion is configured to removably engage the center portion of the main body and wherein the horizontally extending portion comprises a push-surface;
inserting the mouth insert into a buccal cavity of a user's mouth;
placing tongue, teeth or finger of the user onto the push-surface and applying pressure upward to a buccal cavity of the user and towards an anterior portion a nose of the user.

\* \* \* \* \*